United States Patent
Cosman, Jr. et al.

(10) Patent No.: US 10,588,687 B2
(45) Date of Patent: Mar. 17, 2020

(54) COOL RF ELECTRODE

(75) Inventors: Eric R. Cosman, Jr., Belmont, MA (US); Eric R. Cosman, Sr., Belmont, MA (US)

(73) Assignee: COSMAN INSTRUMENTS, LLC, Burlinton, MA (US)

( * ) Notice: Subject to any disclaimer, the term of this patent is extended or adjusted under 35 U.S.C. 154(b) by 930 days.

(21) Appl. No.: 13/153,696

(22) Filed: Jun. 6, 2011

(65) Prior Publication Data
US 2014/0081260 A1    Mar. 20, 2014

(51) Int. Cl.
*A61B 18/14* (2006.01)
*A61B 18/18* (2006.01)
*A61B 18/00* (2006.01)
*A61B 90/00* (2016.01)

(52) U.S. Cl.
CPC .......... *A61B 18/1477* (2013.01); *A61B 18/14* (2013.01); *A61B 18/148* (2013.01); *A61B 18/18* (2013.01); *A61B 2018/00011* (2013.01); *A61B 2018/00023* (2013.01); *A61B 2018/00577* (2013.01); *A61B 2018/1425* (2013.01); *A61B 2090/3925* (2016.02); *A61B 2090/3966* (2016.02)

(58) Field of Classification Search
CPC ........ A61B 18/1477; A61B 2018/1425; A61B 2018/00011; A61B 2019/5425; A61B 2018/00023; A61B 2019/5466
USPC .............................................. 606/41
See application file for complete search history.

(56) References Cited

U.S. PATENT DOCUMENTS

| | | | | |
|---|---|---|---|---|
| 5,571,147 A | * | 11/1996 | Sluijter | A61B 18/1482 604/21 |
| 6,241,725 B1 | * | 6/2001 | Cosman | A61B 18/1477 600/41 |
| 6,506,189 B1 | * | 1/2003 | Rittman, III | A61B 18/1482 606/41 |
| 6,575,969 B1 | * | 6/2003 | Rittman, III | A61B 18/1482 128/898 |
| 2003/0040743 A1 | * | 2/2003 | Cosman et al. | 606/41 |
| 2006/0178666 A1 | * | 8/2006 | Cosman et al. | 606/41 |
| 2008/0015664 A1 | * | 1/2008 | Podhajsky | A61B 18/1477 607/99 |
| 2008/0039909 A1 | * | 2/2008 | Sharkey et al. | 607/96 |
| 2008/0269763 A1 | * | 10/2008 | Bonde et al. | 606/99 |
| 2009/0228005 A1 | * | 9/2009 | Glazer et al. | 606/48 |

* cited by examiner

*Primary Examiner* — Eun Hwa Kim
(74) *Attorney, Agent, or Firm* — Steptoe & Johnson LLP

(57) ABSTRACT

A system and method for applying energy, particularly radiofrequency (RF) electrical energy, to a living body can be used in tissue ablation and includes a combination of cannulas, guidance stylets, and a cooled high-frequency electrode.

61 Claims, 7 Drawing Sheets

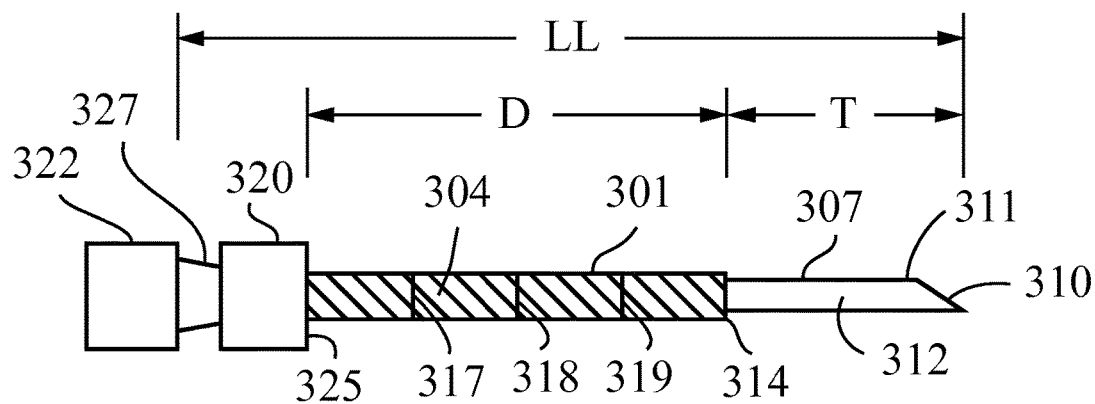
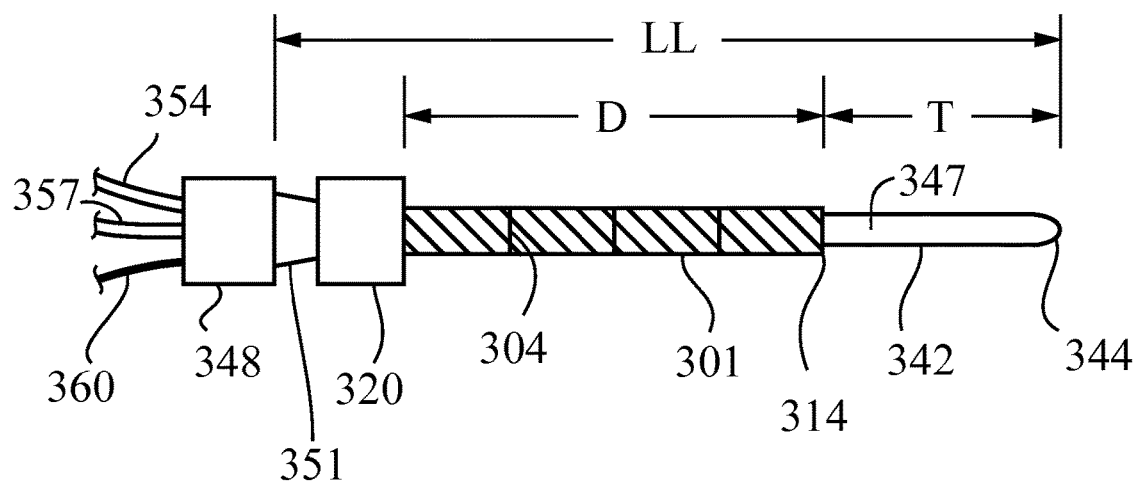
Fig. 3

| 601 | CHOOSE A CANNULA THAT IS AT LEAST PARTIALLY INSULATED AND A STYLET TO BE INSERTED INTO THE CANNULA APPROPRIATE TO INSERT INTO BODILY TISSUE TO APPROACH A SELECTED TARGET TO BE ABLATED, THE STYLET HAVING A KNOWN EXTENSION BEYOND THE DISTAL END OF THE CANNULA. |

| 604 | INSERT THE COMBINATION OF SAID STYLET WITHIN SAID CANNULA INTO THE PATIENT'S BODY SO THAT THE DISTAL PORTION OF THE CANNULA AND OF THE STYLET ARE IN A DESIRED TARGET POSITION IN THE BODILY TISSUE. |

| 607 | REMOVE SAID STYLET FROM SAID CANNULA, AND INSERT AN ELECTRODE INTO SAID CANNULA, THE ELECTRODE HAVING AN UNINSULATED DISTAL END THAT EXTENDS BEYOND THE DISTAL END OF THE CANNULA BY THE SAME KNOWN EXTENSION AS FOR THE STYLET, AND THE ELECTRODE HAVING AN INTERNAL COOLING CHANNEL AND CONNECTION PORTS TO ENABLE FLOW OF COOLANT FLUID THROUGH THE ELECTRODE TO COOL THE UNINSULATED DISTAL END OF THE ELECTRODE. |

| 612 | CONNECT SAID ELECTRODE TO A HIGH-FREQUENCY GENERATOR SO THAT THE OUTPUT SIGNAL OF THE GENERATOR IS CONNECTED TO THE UNINSULATED DISTAL END OF THE ELECTRODE, AND TO CONNECT SAID ELECTRODE TO A SOURCE OF COOLANT FLUID CAN FLOW BE COOLANT FLUID THROUGH THE ELECTRODE TO COOL SAID UNINSULATED DISTAL END OF THE ELECTRODE. |

| 616 | APPLY SAID OUTPUT SIGNAL TO SAID ELECTRODE TO CAUSE ABLATED HEATING OF THE BODILY TISSUE NEAR SAID COOLED INSULATED DISTAL END OF THE SAID ELECTRODE. |

FIG. 6

COOL RF ELECTRODE

TECHNICAL FIELD

This invention relates generally to the advances in medical systems and procedures for prolonging and improving human life. The present invention relates generally to a system and method for applying energy, particularly radiofrequency (RF) electrical energy, to a living body. The present invention also relates generally to a system and method for apply energy for the purpose of tissue ablation.

BACKGROUND

The theory behind and practice of RF heat ablation has been known for decades, and a wide range of suitable RF generators and electrodes exists. For example, equipment for causing heat lesions is available from Radionics, Inc., located in Burlington, Mass. A research paper by E. R. Cosman, et al., entitled "Theoretical Aspects of Radio Frequency Lesions in the Dorsal Root Entry Zone," *Neurosurgery*, Vol. 15, No. 6, pp. 945-0950 (1984), describes various techniques associated with radio frequency lesions and is hereby incorporated by reference herein in its entirety. Also, research papers by S. N. Goldberg, et al., entitled "Tissue Ablation with Radio Frequency: Effect of Probe Size, Gauge, Duration, and Temperature on Lesion Volume," Acad. Radiol., Vol. 2, pp. 399-404 (1995), and "Thermal Ablation Therapy for Focal Malignancy," AJR, Vol. 174, pp. 323-331 (1999), described techniques and considerations relating to tissue ablation with radio frequency energy and are hereby incorporated by reference herein in its entirety.

Examples of high frequency generators and electrodes are given in the papers of entitled "Theoretical Aspects of Radiofrequency Lesions and the Dorsal Root Entry Zone," by Cosman, E. R., et al., *Neurosurg* 15:945-950, 1984; and "Methods of Making Nervous System Lesions," by Cosman, E. R. and Cosman, B. J. in Wilkins R. H., Rengachary S. S. (eds): *Neurosurgery*, New York, McGraw-Hill, Vol. III, pp. 2490-2498, 1984, and are hereby incorporated by reference herein in their entirety.

The use of radiofrequency (RF) generators and electrodes in neural tissue for the treatment of pain and functional disorders is well known. Included herein by reference, an as an example, the RFG-3C Plus RF Generator of Radionics, Inc., Burlington, Mass., and its associated electrodes are used in the treatment of the nervous system, and the treatment pain and functional disorders. The RFG-3C Plus generator has one electrode output jack for connection to a single active electrode, and it has one reference electrode jack for connection to a reference electrode. When the active electrode is inserted into the body, and the reference electrode is placed, typically on the patient's skin, then RF current form the RF generate flows through the patient's body between the two electrodes. The generator can be activated and its signal output can be applied between the electrodes. Typically, this is referred to as a monopolar configuration because the active electrode is of smaller area than the reference electrode, and so the concentration of RF current is highest near it and the action of the RF electric field, whether for heating or for pulsed RF field therapy is greater there. This usually referred to as a single electrode configuration since there is only one "active" electrode. Parameters that can be measured by the RFG-3C Plus RF generator include impedance, HF voltage, HF current, HF power, and electrode tip temperature. Parameters that may be set by the user include time of energy delivery, desired electrode temperature, stimulation frequencies and durations, and level of stimulation output. In general, electrode temperature is a parameter that may be controlled by the regulation of high frequency output power. Existing RF generators have interfaces that allow the selection of one or more of these treatment parameters, as well as various methods to display the parameters mentioned The use of high frequency electrodes for heat ablation treatment of functional disease and in the destruction of tumors is well known. One example is the destruction of cancerous tumors of the kidney using radio frequency (RF) heat ablation. A paper by D. W. Gervais, et al., entitled "Radio Frequency Ablation of Renal Cell Carcinoma: Early Clinical Experience," Radiology, Vol. 217, No. 2, pp. 665-672 (2000), describes using a rigid tissue perforating and penetrating electrode that has a sharpened tip to self-penetrate the skin and tissue of the patient. This paper is hereby incorporated by reference herein in its entirety.

Four patents have issued on PRF by Sluijter M. E., Rittman W. J., and Cosman E. R. They are "Method and Apparatus for Altering Neural Tissue Function," U.S. Pat. No. 5,983,141, issued Nov. 9, 1999; "Method and System for Neural Tissue Modification," U.S. Pat. No. 6,161,048, issued Dec. 12, 2000; "Modulated High Frequency Tissue Modification," U.S. Pat. No. 6,246,912 B1, issued Jun. 12, 2001; and "Method and Apparatus for Altering Neural Tissue Function," U.S. Pat. No. 6,259,952 B1, issued Jul. 10, 2001. These four patents are hereby incorporated by reference herein in their entirety.

United States patents by E. R. Cosman and W. J. Rittman, III, entitled "Cool-Tip Electrode Thermal Surgery System," U.S. Pat. No. 6,506,189 B1, date of patent Jan. 14, 2003, and "Cluster Ablation Electrode System," U.S. Pat. No. 6,530,922 B1, date of patent Mar. 11, 2003, and "Cool-Tip Radiofrequency Thermosurgery Electrode System For Tumor Ablation", U.S. Pat. No. 6,575,969 b 1, date of patent Jun. 10, 2003, describe systems and methods related to tissue ablation with radiofrequency energy and electrodes and are hereby incorporated by reference herein in their entirety. One electrode system described in these patents comprises an electrode with an insulated shaft except for a fixed uninsulated tip exposure of an uninsulated exposed length, the electrode being internally cooled so that the uninsulated exposed tip is cooled. The electrode shaft is a rigid and self tissue piercing with a sharp pointed distal tip on the electrode shaft. This is essentially the configuration of cooled electrode offered by the Radionics Cool-Tip Electrode System (Radionics, Inc., Burlington Mass.) and the Valley Lab Cool-Tip Electrode System (Valley lab, Inc., Boulder Colo.) that are described later in this section. This design of electrode has one disadvantage that the initial insertion of the electrode can encounter tissue resistance which will displace the target volume, for example against a firm cancerous tumor, making it difficult to accurately position the electrode tip at the desired target tissue. It has another disadvantage that the clinician must inventory a multiplicity of electrodes having different lengths of tip exposure to accommodate his needs to create ablation volumes of different sizes, for example, to accommodate different sizes of tumors to be ablated. Another electrode system described in these patents comprises a system of a fully insulated cannula, a pointed stylet that can be inserted into the cannula so that the sharpened tip of the stylet just emerges from the distal tip end of the cannula when the stylet hub engages the cannula hub, and a separate cooled uninsulated electrode that can be inserted into the cannula when the stylet has been removed. The electrode length is greater than the stylet length so that the distal end of the electrode extends beyond the end of the cannula distal tip by a predetermined length when the hub of the electrode engages with the hub of the cannula, and the amount that it extends beyond the cannula tip is greater than the amount that the stylet extends beyond the cannula tip when the stylet is inserted into the cannula. One disadvantage of this electrode system design is that the stylet does not protrude to an equal degree beyond the cannula tip as the electrode, so that the pointed stylet does not produce a tract in the target tissue that can facilitate insertion of the electrode tip to the desired target. Another disadvantage is that the sharp stylet does not extend significantly from the distal end of the cannula, so that the cool electrode when inserted into the cannula, after the stylet has been removed, must push through and penetrate the bodily tissue until the distal tip of the cool electrode reaches a desire to target position within the tissue, for example, at an appropriate point inside a tumor that is to be ablated.

The Cosman G4 Radiofrequency generator (Cosman Medical, Inc., Burlington, Mass.) is another example of a modern RF lesion generator and the brochure printed in 2011 is hereby incorporated by reference herein in its entirety.

The Radionics Cool-Tip Electrode System (Radionics, Inc., Burlington Mass.) and the Valley Lab Cool-Tip Electrode System (Valley lab, Inc., Boulder Colo.) are existing examples of cooled radiofrequency electrodes designed to ablate tissue in the living body, an example of which is ablation of tumors. The brochures for these products are hereby incorporated by reference herein in its entirety. These electrodes systems comprise an electrode that has a partially insulated shaft, an uninsulated distal tip of known uninsulated length, and the distal tip is sharpened so that the electrode can pierce tissue and the bodily tissue to be positioned in a target position in the living body. The uninsulated tip, and the electrodes connected to the output signal of a high frequency generator, will produce heating of the bodily tissue near the tip. The electrodes are also cooled by an internal fluid cooling system, and this has the effect of producing larger ablation volumes which can be desired, for example, to coagulate large tumors. One disadvantage of these electrodes is that they are supplied sterile packaged and have a fixed uninsulated tip of a known length. This means that the manufacture and the hospital user must inventory a range of these electrodes with various lengths and tip exposures to accommodate a tumor size related to a specific patient. Another disadvantage space is that the sharpened distal end is in the shape of a trocar point, and this produces a significant resistance force when inserting the tissue piercing electrode into the bodily tissue. This can cause displacement of the tissue, especially full firm tissue and for firm tumor target volumes. A further disadvantage of these electrodes is that they have large hubs which are greater than 15 mm in diameter and are several inches in length. These large hubs are necessary according to the design so that the clinician can have sufficient manual grip on the hub to implement the forceful self piercing and penetration manipulation of the electrode through the patient's skin and fur the wrong into the target volume within the bodily tissue, as for example, into a cancerous tumor that is deep within the body. This disadvantage means that the electrode systems are bulky and present a heavy and large hub structure. this can have the disadvantaging of producing undesired torque and forces on the electrode when inserted into the body causing potential inaccuracy and shift of positioning the electrode distal tip with respect to a desired target position in the tissue. The large and bulky hubs have another disadvantage that is more difficult to insert multiple independent electrodes into the body in a tight cluster, because the large hub diameter limits the closeness with which the electrodes and the hubs can be clustered. In one case, this can be disadvantageous when multiple electrodes are being passed between the space between the ribs to access, For example, a cancerous tumor in the liver or in the lung.

In a patent by Mark Leung, et al., entitled Electrosurgical Tissue Treatment Method, U.S. Pat. No. 7,294,127 B2, date of patent: Nov. 13, 2007; and, in another patent by Mark Leung, et al., entitled Electrosurgical Tissue Treatment Method, US patent number 2005/0177210 A1, date of patent: Aug. 11, 2005, a cooled RF electrode is shown for an application in the field of pain therapy for bipolar lesion making in the spine. These patents are hereby incorporated by reference herein in its entirety. The Baylis Medical Company offers a commercial version of the design shown in the patent these two patents, and the brochures for these products are hereby incorporated by reference herein in its entirety. These two patents and the Baylis product describes a system of an insulated cannula with introducing stylet that emerges by a few millimeters from the distal end of the cannula, and substantially less than 10 mm. A high-frequency electrode can be inserted into the cannula, when the introducing stylet has been removed, and the electrode has a distal end which emerges from the end of the cannula when the hub of the electrode in the cannula hub are engaged together. The distal end of the electrode will emerge from the distal end of the cannula by a different distance than the distance that the distal end of the stylet from the cannula when the stylet is inserted into the cannula. In one electrode system of the Baylis products, the TransDiscal electrode, the high-frequency electrode also is adapted so that its distal portion that emerges beyond the distal end of the cannula has a partially insulated portion, and has an uninsulated exposed distal tip of the electrode that is approximately 6 mm in length. In the Baylis products referred to by Baylis as Sinergy, Transdiscal, and Thoracool, the length of the uninsulated exposed conductive tip portion that is used to energize the tissue around the tip is between 4 and 6 mm. When the electrode is connected to the output signal of a high-frequency generator, it is the uninsulated exposed distal tip of the electrode which is used to create the thermal ablation. In all Baylis products, the high-frequency electrode shaft is completely insulated over the entirety or almost the entirety of the portion of the shaft that is inside the cannula, when the electrode hub is fully engaged with the cannula hub. One disadvantage of this design is that it either does not, or does not reliably, enable high frequency output signal to be conducted between the electrode and the cannula. The cannula that is being used is insulated over its entire length, including right up to the distal tip end, so that the cannula does not have any uninsulated portion to energize tissue that surrounds the cannula when the cannula is inserted into bodily tissue. As a consequence, when the electrode is connected to the output signal of a high-frequency generator, the cannula itself does not deliver any output signal to the tissue in which it is placed. The high-frequency electrode is also cooled by an internal fluid channel's that carry cooled fluid from a fluid supply external to the electrode that can be connected to the electrode by tubes. The electrode of these designs has a hub which has a diameter of greater than 13 mm. One disadvantage of TransDiscal Baylis electrode design is that the portion of the electrode that emerges from the cannula is not completely uninsulated. Another disadvantage of this design is that the cannula is completely insulated preventing thermal ablation over the portion of the cannula shaft distal tip. Another disadvantage of this design is that the high-frequency electrode does not make reliable electrical contact with the cannula when the electrode is connected to a high-frequency generator. The design of the fluid channel's in the electrode hub of the devices shown the two referenced patents and in the Baylis brochures comprise input and output fluid tubes into the hub structure in the input and output fluid tubes are connected to fluid carrying tubes that extend inside the electrode shaft and down to the distal end of the electrode shaft. This design has the disadvantage that the input and the output tubes are incorporated within the hub structure, and the inflow and the outflow internal tubes within the electrode shaft occupying a lateral displacement equal to the sum of the diameters of the internal tubes. These factors have the disadvantages that the hub diameter of the Baylis cooled RF electrode is 13 mm. This has the disadvantage that the diameter is sufficiently large that it restricts the use of multiple such Baylis electrodes in a cluster where the electrodes are inserted into the tissue in a parallel array with the distance between the hubs less than 13 mm. Another disadvantage is that the cooling efficiency at the tip of the high-frequency electrode is reduced by the fluid impedance of the two internal tubes that extend inside and along the entire length of the electrode shaft. Another disadvantage is that the Baylis electrode designs is that they have an exposed electrode tip length of only approximately 4 to 6 mm, and this is insufficient for ablation of large target volumes such as large cancerous tumors which can be, in a in typical cases greater than 1 cm in dimension, and in other typical cases up to 4 cm, or 5 cm, or more in dimension. In all of the Baylis products, the electrode shaft comprises a plastic tube with delicate flexible cooling tubes within. Only over approximately up to 6 mm of the distal tip end if the shaft's outer material a conductive metal. This has one disadvantage that the shaft is not robust to high longitudinal or pushing force is as the electrode is passed into bodily tissue. Another disadvantage of the plastic shaft is that it is not robust to lateral bending forces.

A wide variety of radiofrequency electric configurations are offered by Cosman Medical, Inc. One example is the TIC Kit which comprises for equal length cannulas, each having different and known uninsulated distal tip lengths. The Kit also comprises a stylet which can be inserted into each cannula to produce a sharpened occluded tip for the combination of the cannula with the stylet when the stylet is inserted into the cannula so that the hub of the cannula and the hub of the stylet are engaged with each other. The Kit also includes a fully uninsulated high frequency electrode that can be inserted into each of the cannula, when the stylet has been removed, so that when the electrode is connected to the output signal of a high-frequency generator, then the output signal will energize the uninsulated distal tip of the cannula. The electrode has an indwelling temperature sensor in its distal tip so that when the electrode is inserted into the cannula with the hub of the electrode is engaged with the hub of the cannula, the temperature sensor will measure the heating temperature corresponding to heating of the tissue around the uninsulated tip of the cannula. This electrode system was designed for coagulation of the trigeminal nerve to treat trigeminal neuralgia. One disadvantage of this design is that electrode system is not adapted to be cooled by an internal cooling fluid, so this system is not suitable for ablation of large target volumes such as for cancerous tumors. Another disadvantage of this design is the uninsulated exposed distal tip lengths of the cannula are not greater than 10 mm, which is not adequate for most ablations of cancerous tumors.

The present invention overcomes the stated disadvantages and other limitations of the prior art.

SUMMARY OF THE INVENTION

In one exemplary embodiment, the present invention is directed towards systems and methods for ablating tissue in the living body. This can include using a combination of insertion cannulas, rigid guidance stylets be inserted into the cannulas during initial placement in the body tissue, and a cooled high-frequency electrode that can also be inserted into the cannulas after the stylet has been removed and the cannula is appropriately placed in the direction towards a decided target volume in the bodily tissue. The cooled high-frequency electrode is adapted for creating large ablation volumes. In one application, the present invention is directed towards thermal tissue ablation including ablation of cancerous tumors.

The present invention, in one example, is directed towards a system of cannulas that can be directed percutaneously towards a target volume within the bodily tissue and guided by a rigid pointed tissue piercing stylet that can be inserted into the cannula, and a high-frequency electrode that can alternatively be inserted into the cannulas to produce thermal ablation volumes in the tissue of the living body. In one example the electrode can be a cooled electrode. In another example the electrode is a non-cooled the electrode.

In one embodiment, a high-frequency cooled electrode can have a slender diameter hub structure of about 10 mm or less to enable the use of multiple probes to be passed through multiple cannulas that are inserted towards a target volume in a tight spatial cluster to create a larger ablation volume, as for example, for the destruction of a large cancerous tumor. One advantage of this design is that it enables close clustering of the cannula/electrode combination. Another advantage is that by using a pointed stylet to be inserted into the cannula initially for the placement of the cannula/stylet combination into the target volume, wherein, for example, the distal tip of the stylet relative to the cannula is the same as the distal tip of the high-frequency electrode relative to the cannula, less force needs to be applied on the hub of the electrode to push it into the target volume because the rigid pointed stylet has produced a tract through the bodily tissue prior to insertion of the electrode into the stylet. This has the advantage that small diameter, shorter length, and more compact hub structures for the electrode can be used because less manual force is required for initial insertion of the electrode/cannula combination to achieve the target volume. The present invention describes several embodiments of such cannula/guidance stylets/electrode configurations to achieve this advantageous objective which overcomes the disadvantages of electrode systems in the prior art.

In one embodiment of the present invention, a system of cannulas of different lengths are used in combination with a sharpened guidance stylet or a needle type stylet, which for example can be a pointed needle with its own internal stylet or a solid sharpened metal rod, which are adapted so that when the guidance stylet/needle is inserted into each of the cannulas with the hub of the stylet engage with the hub of the cannula, then the distal tip of the stylet extends beyond the distal tip of the cannula by a known and/or predetermined length, and the combination of cannula with inserted stylet can be pushed easily into the bodily tissue so that the tip of the stylet can be positioned at a desired target location. In one embodiment, a high-frequency electrode, having substantially the same length as the stylet, can be inserted into the cannula, when the stylet has been removed, and the electrode distal end extends beyond the cannula distal end by the same known and/or predetermined length as the stylet extends beyond the cannula distal end when it is inserted into the cannula. In one example, the portion of the electrode that extends beyond the cannula distal end is uninsulated. When inserting the electrode into the cannula after the cannula has been positioned and direct it into the body to use of the stylet/cannula combination, the electrode tip can reach a desired target tissue in the bodily tissue by following along the insertion tract made by the guidance stylet. One advantage of this configuration is that it comprises a single length of guidance stylet, and a single length of high-frequency electrode, and, in one example, a multiplicity of cannulas of different lengths so that different lengths of exposed electrode tip can be achieved within the bodily tissue to accommodate patient specific clinical needs and objectives. This has one advantage that the appropriate cannula can be selected to accommodate the desired ablation volume according to the size of the target volume to be ablated, for example, the size of a cancerous tumor to be ablated. Another advantage is that using one combined set of a multiplicity of cannulas, a single guidance stylet, and a single high-frequency electrode, the clinician can select the appropriate a cannula for a desired length of electrode tip exposure beyond the end of the cannula. Another advantage is that the guidance stylets can have a conventional beveled needle point which is extremely sharp and facilitates tissue piercing and penetration into even the toughest bodily tissues. This means that the initial insertion of the cannula with a stylet in place can be made very easily and with reduced pushing and manipulative force by the clinician. Then subsequently, a high-frequency electrode can be passed to the cannula, when the stylet is removed, for easy passage of the electrode to the target volume by the electrode following along the tract of the initial stylet insertion. This has one advantage that less force has to be inserted on a high-frequency electrode as it is being inserted. This overcomes one disadvantage of the cooled electrode systems of the prior art which have a fixed tip exposure for each high-frequency electrode which means that a clinician must inventory and stock a multiplicity of these expensive electrodes to accommodate patient specific geometries of target volumes that are to be ablated. It also overcomes another disadvantage of the prior art cool electrode systems, that the delicate high-frequency electrode does not have to have a tissue piercing pointed tip. It also overcomes another disadvantage of the prior art cooled electrode systems which have a trocar type pointed tip on the high-frequency electrode, which is less well adapted to easy tissue piercing and insertion into tough bodily tissues and therefore acquires more pushing and manipulation forces on the prior art electrode systems for insertion into the body. A consequent disadvantage of the cooled electrodes of the prior art is that they have hubs that are made larger than 15 mm in diameter and have a large physical size and weight to accommodate the increased pushing force required to the insert them into the tissue of the body. This makes it disadvantageous to easily place and insert of clusters of cooled electrodes of the prior art into a target volume, such as a tumor, for the purpose of making a large ablation volume. Another advantage of the present invention is that fluids, such as anesthetics and coagulants, can be injected through the introducer cannula either before or after the application of high-frequency output.

In one embodiment of the present invention, a system comprising a cannula or cannulas, a tissue piercing guiding stylet, and a high-frequency electrode are adapted so that the length of the stylet and the length of the electrode are substantially the same so that when each of the stylet or the electrode is inserted into any one of the cannula or cannulas, so that the hub of each of the stylet or the hub of the electrode engages with the hub of the cannula, the distal tip of the stylet and the distal tip of the electrode will be at the same position relative to the distal end of the cannula. One advantage of this design is that the combination of the cannula and sharpened stylet can be inserted into the bodily tissue so that the distal tip of the stylet reaches a desired target position within the tissue, and then when the stylet is removed from the cannula, the electrode can be inserted into the cannula, and the distal tip of the electrode will then be at essentially the same desired target position as was the distal tip of the stylet when it was inserted into the cannula. One advantage of this design is that the sharpened stylet can act as a guide to produce a tract into the tissue prior to the insertion of the electrode into the cannula, and therefore so that less force will be needed to be applied to the electrode to the bodily tissue so that the electrodes distal tip is at a desired target position. This overcomes a disadvantage of the cooled electrodes of the prior art cited above wherein the cooled electrode has a sharp point and must be pushed through a virgin path through the bodily tissue, which requires a substantial manual force to be applied to the electrode during that pushing process.

In one embodiment of the present invention, a system comprising a set of one cannula or multiple cannulas, a tissue piercing guiding stylet, and a high-frequency electrode are adapted so that the shaft of the cannula has an insulated portion and an uninsulated cannula distal tip portion of known length, for a single cannula, or known different lengths, for multiple cannulas, and a tissue piercing stylet can be inserted into the cannula or cannulas so that the combination of the stylet and the cannula has a tissue piercing sharpened point, and the high-frequency electrode is uninsulated over at least a portion of its shaft length so that makes electrical contact with the cannula or cannulas uninsulated distal tips, and the electrode is adapted to be cooled internally so that when inserted into said cannula or cannulas will cool the uninsulated distal cannula tip, and when said electrode is connected to a high-frequency generator, the output signal of the generator will be connected through the electrode to the uninsulated cannula distal tip. One advantage of this system is that there is one guidance stylet and one high-frequency electrode in combination with either one cannula all with multiple cannulas so that a known uninsulated portion of the cannula or multiple known uninsulated portions of the cannulas can be used to produce a desired known conductive tip length for tissue ablation, which, in one example, can be approximately length of the desired tissue ablation volume. One advantage is that the stylet with the cannula can be used to produce the tissue piercing tract, and therefore there can be less manual pushing force applied to the electrode when it is inserted into the cannula so that the tip of the electrode achieves essentially the same position relative to the distal tip of the cannula as the position of the stylet relative to the distal tip of the cannula when the stylet is inserted into the cannula. Another advantage of the system is that a clinician can be offered multiple cannulas with different uninsulated distal tip lengths, together with a single insertion stylet and a single high-frequency electrode, and the clinician can select the cannula distal tip length which is appropriate for producing a desired ablation volume around the uninsulated cannula tip. This has the advantage of fewer parts to be inventoried by the clinician in the hospital. It also overcomes the disadvantage cooled electrode systems of the prior art cited above wherein clinician or hospital has to inventory in sterile stock multiple high-frequency electrodes of different uninsulated tip lengths which is inefficient and expensive since the high-frequency electrode itself is the most expensive part of the systems. Another advantage of one embodiment of this system is that the selected cannula couples to the electrode in a pre-determined, rigid manner. Another advantage of one embodiment of this system is that the electrode and cannula can be coupled without the use of a set screw or other adjustable device that involves an additional manipulation in order to set the uninsulated tip exposure length.

One objective of the present invention is to provide a system of separable cannula or cannulas, a guidance stylet that can be inserted into the cannula or cannulas, and a high-frequency electrode that can be inserted into the cannula or cannulas to provide a separate tissue piercing guidance system of the cannula or cannulas together with the sharpened stylet for initial access into the bodily tissue to be directed towards a desired target volume or target position, and then to be able to remove the stylet from the cannula or cannulas and insert the high-frequency electrode into the cannula or cannulas so that when the hub of the electrode and the hub of the cannula are engaged in a known relative position to each other, the distal tip of the electrode will be directed towards the desired target volume or target position in the same way as was the stylet when it was inserted into the cannula or cannulas. One advantage of the system is that the combination of cannula or cannulas together with the stylet provides an entrance tract into the bodily tissue during the initial insertion process. Another advantage is that less manual pushing force will be required to be applied to the electrode when it is inserted into the cannula to achieve a desired target position compared to a system of the prior art wherein the electrode itself has a sharpened tissue piercing point which must be pushed into the bodily tissue.

A further embodiment of the present invention comprises a method and process of utilizing a set of one or more cannulas, an introducing stylet, and a high-frequency electrode to provide an access of the cannula with the stylet inserted in the cannula to be directed towards a desired target volume within the bodily tissue, and utilizing a high-frequency cooled electrode to be inserted into each of the one or more cannulas so that the electrode distal tip is positioned is substantially the same location relative to the distal tip of the cannula as is the distal tip of the stylet relative to the distal tip of the one or more cannulas when the stylet is inserted into the wild more cannulas.

The invention can be used in numerous organs in the body, including the brain, spine, liver, lung, bone, kidney, abdominal structures, etc., and for the treatment of cancerous tumors, other pathological target volumes, or other types of tissue target volumes in, for example, nervous tissue, bone tissue, cardiac tissue, muscle tissue, or other types of bodily tissues.

The details of one or more embodiments of the invention are set forth in the accompanying drawings and description below. Other features, objects and advantages of the invention will be apparent from the description and drawings and from the claims.

BRIEF DESCRIPTION OF THE DRAWINGS

In the drawings that constitute a part of the specification, embodiments exhibited various forms and features hereof are set forth, specifically:

FIG. 3 is a schematic diagram in side elevation view showing a system of a cannula that has an insulated shaft, a stylet and/or needle with a tissue piercing point that can be inserted into the cannula end extends a distance out of the distal end of the cannula when the hubs of the cannula and stylet engage, and a cooled uninsulated high-frequency electrode that can also be inserted into the cannula end extends the same distance out of the distal end of the cannula as does the stylet when the hubs of the cannula and electrode engage.

FIG. 6 is a flow chart of a process of inserting of an insulated and/or partially insulated cannula together with a tissue piercing guidance needle and/or stylet system, followed by insertion of a high-frequency electrode into the cannula for the purpose of thermal ablation of the target volume.

DETAILED DESCRIPTION OF THE INVENTION

Figure 1A:
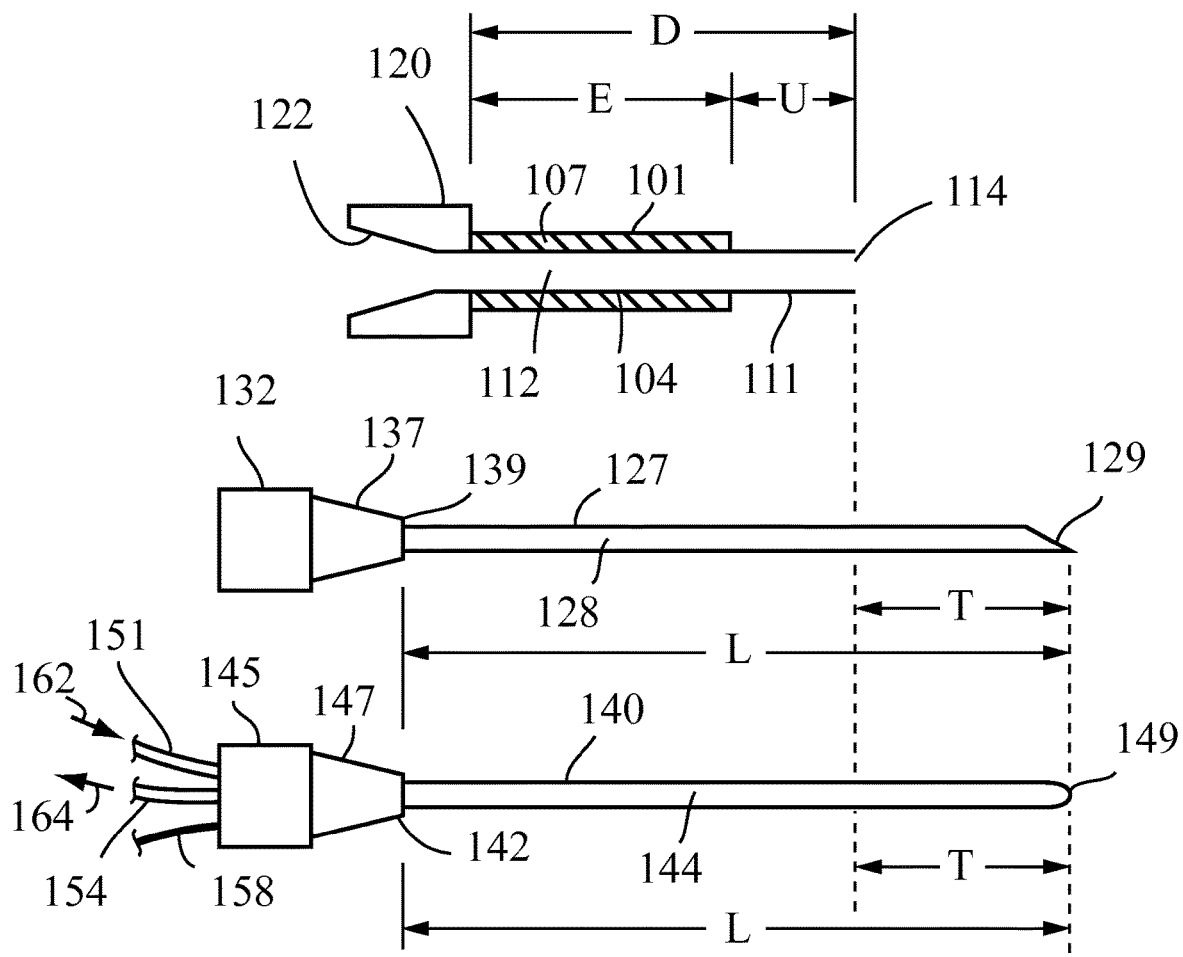
FIG. 1A is a schematic diagram, in side elevation view, showing an insertion, guidance, and electrode system comprising a partially insulated cannula shown in sectional view, an introducing stylet with a sharpened point shown in side elevation view, and a high-frequency electrode that can be internally cooled shown in side elevation view.

Referring to FIG. 1A, an electrode system for tissue ablation in accordance with the present invention is shown in schematic representation, comprising at least one cannula, a guidance stylet and/or needle that can be inserted into the cannula, and a high-frequency electrode that can also be inserted into the cannula, when the guidance stylet is removed. The cannula as shown in sectional side elevation view and has a shaft 101 of length D. In one example, the cannula shaft 101 has a proximal portion 107, represented by the hatched area, of length E that is insulated and the distal portion 111 of length U that is uninsulated. On the proximal end, the cannula shaft is connected to a hub 120. The hub can have engagement surface or shoulder represented by 122, which, for example, in one embodiment can be a luer taper. The cannula has an opening 112 through it, the opening 112 connecting to an opening in the distal tip 114. In one example, the distal tip 114 can be a squared off end. In another example the distal tip opening 114 can have a beveled or tapered configuration. In one example, the cannula can be comprised of a metal tube 104 that is part of the cannula shaft 101. In one example, the metal tubing 104 can be, for example, a stainless steel tubing or other metal material that this conductive. In one example, the uninsulated distal portion of the shaft can have a length U that is nonzero. In another example, the uninsulated portion of the cannula shaft can have a length U that is essentially zero in length, and therefore, in that example, the insulated portion 107 has a length E that is substantially equal to the external length D of the shaft. In one example the uninsulated length U and the overall shaft length D can be known and predetermined, and suited and adapted for insertion into the bodily tissue to a certain length to accommodate clinical needs, such as for example approaching a cancerous tumor volume at a certain depth beneath the skin. In another example, the system of FIG. 1 can include multiple cannulas each of which have different uninsulated tip lengths U to accommodate clinical needs. For example, if the uninsulated portion 111 is used to energize tissue near it with high frequency output signal, when the cannula is inserted into bodily tissue, a selection of cannulas with differing tip lengths U can be useful to match the volume of ablation that is desired. Another example, the embodiment can comprise multiple cannula each with different shaft lengths D to accommodate different total uninsulated tip exposure when the high frequency electrode is inserted into the cannula, and/or different depths of penetration of the cannula shaft when it is inserted into bodily tissue.

Referring FIG. 1A, a stylet structure 127 is shown in side elevation view and is adapted to be inserted into the lumen 112 of the cannula 101. The stylet structure has a shaft 128 which has a nominal length L. The shaft 128 can pass through the lumen opening 112 in the cannula. In one example, the stylet shaft 128 is uninsulated and is made of conductive material, such as, in one example, a solid metal shaft. In another example the shaft 128 can comprise a needle structure that includes a hollow sharp and pointed needle with its own obdurating inner stylet. In one example, it has a distal tip 129 which has a sharpened tissue piercing point. In one example, it has a hub structure 132 which comprises a Luer taper surface 137 that is adapted to engage, in one example, with the luer engagement surface 122 of the at least one cannula 101. In one example, the stylet structure 127 is adapted so that when it is inserted into the cannula 101, and the hub 132 of the stylet structure engages with the hub 120 of the cannula, then the uninsulated exposed conductive surface of the shaft 128 extends beyond the distal tip 114 of the cannula by the distance T. The length L of the stylet structure and the length D of the cannula can be predetermined and/or selectable so that the degree of tip extension length T of the stylet structure beyond the distal end of the cannula 114 is a known, and/or predetermined/ and/or selectable length to accommodate the clinical needs for a given patient and a given target structure objective.

Referring to FIG. 1A, a high-frequency electrodes 140 is shown inside elevation view. The electrode comprises an electrode shaft 144 which has a proximal end and has a distal end which terminates in a distal tip 149. In one example, the electrode shaft 144 is completely uninsulated. In one example, it can comprise a metal tubing, such as, for example, a stainless steel tubing. In another example, the electrode shaft can comprise a conductive material. In another example, the electrode shaft can be partially insulated. In another example, the electrode shaft can include plastic and other non-conductive materials. The electrode can be adapted to be inserted into the through-opening 112 of the cannula 101, when the stylet 127 is removed from the cannula 101. In one example, the hub can comprise a luer tapered 147 which is adapted to engage, in one example, a luer engagement surface 122 of the cannula hub 120. The electrode has a connection 158 which can be a cable or wire connection that is adapted to be connected to a high frequency generator so that the output signal of the high frequency generator can be connected to the uninsulated portion of the electrode shaft 144. Therefore, when the electrode 140 is inserted into the cannula 101, and when the cannula shaft comprises a metal tubing 104, and when the output signal from the generator is connected to the shaft 144, in one example, than the exposed conductive electrode shaft 144 can make electrical contact with the cannula metal tubing shaft 104 so that the output signal can be connected thereby to the exposed an insulated cannula distal tip 111. in one example, electrode 140 can have a non-cooled electrode shaft 144. In one example, electrode 140 can have an internal cooling channel so that the shaft of the electrode 144 can be cooled by a cooling fluid running inside the internal cooling channel. In one example not shown explicitly in FIG. 1A, electrode 140 can have an internal cooling channel and an aperture at its distal end so that some or all of the cooled fluid, such as sterile saline or sterile water, enters the tissue in which the electrode is placed. A cooling fluid can flow into the electrode by an input tube 151, and the cooling fluid can flow out of the electrode by an output to 154, the arrows 162 and 164 representing schematically the direction of input and output flow of the cooling fluid into those tubes, respectively. The cooling fluid can be supplied by an external coolant supply, not shown in this figure, which is similar to that used in the cool the RF electrodes systems of the prior art referred to in the BACKGROUND section above. In one example electrode, 140 can have an internal temperature sensor within the shaft 144 at a selected position in the shaft which, for example in one embodiment can be near the distal tip 149. In one example, the distal tip 149 can be a non-tissue piercing shape, for example, a bullet shaped, or a hemispherical shape, or a blunt conical pointed shape, or other shape that does not have a sharp tissue piercing profile. In another example, the electoral distal tip 149 can have a tissue piercing sharpened shape such as a trocar shape, or in another example a needle bevel type shape such as a sharpened tri-cut needlepoint.

Referring to FIG. 1A, in one example, the stylet shaft length L of the stylet structure and the length of the electric shaft 144 shown in FIG. 1A is also L. In this example, the shaft lengths of the two structures, the stylet structure and the electrode structure are substantially equal as shown in FIG. 1A. The length L can, for example, be measured in the case of the stylet from the distal edge 139 of the hub luer surface 137 to the very distal end of the pointed tip 129. Some variation of this length L can, for example, involve measuring to the midpoint of the bevel edge 129. The length L as measured on the electrode 140 can, in one example, be from the distal end 142 of the luer engagement surface 137 to the very distal tip and 149.

Figure 1B:
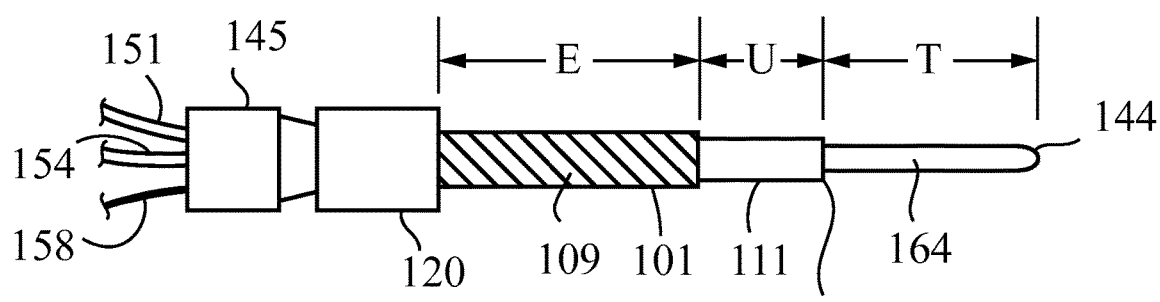
FIG. 1B is a schematic diagram, in side elevation view, of the same electrode system as in FIG. 1A showing the high-frequency electrode inserted into the cannula with the hub of the electrode engaged with the hub of the cannula.

Referring to FIG. 1B, a side elevation view is shown of the combination of the electrode 140 inserted into the cannula 101 so that the electrode hub 145 engages with the cannula hub 120. The insulated portion of the cannula shaft is 109 as indicated by the hatched area. The exposed uninsulated tip in this example comprises the combined uninsulated length of the cannula distal expos tip 111 which has length U together with the portion of the electrode shaft 144 that extends beyond the cannula distal opening 114, that extension portion of the electrode being designated as 164 in FIG. 1B and being specified as having length T in FIG. 1B. Therefore, the combined uninsulated exposed tip in this example is a combination of portion 111 of the cannula and the portion 164 of the electrode, meaning that the length of the total exposed tip is the sum of U plus T. when the electrode shaft 144 is connected to the output signal of a high frequency generator by the wired connection 158, then the electrical connection of the electrode to the metal cannula tubing means that the entire exposed tip, 111 and 164, are connected to the output signal of the high frequency generator. In one example, if the output signal of the high frequency generator is specified as voltage V, and that voltage will be connected to the combined expose tip 111 plus 164 having length U plus T. In one example, if electrode 140 is cooled by in total fluid as described above, then the entire combined exposed conductive tip will be cooled because of the thermal contact between the electrode shaft 144 and the cannula shaft 104.

Referring to FIG. 1A and FIG. 1B, because the shaft length of the stylet structure and the shaft length of the electrode are both substantially equal to the length L, then the degree of extension T of the stylet distal end from the distal end 114 of the cannula when the stylet is inserted into the cannula so that the stylet hub in and engaged with the cannula hub is substantially the same as the degree of extension T of the electrode shaft beyond the distal end of the cannula. Therefore, when the stylet 127 is inserted into the cannula 101, than the combined system can be manually percutaneously pierced and penetrated through the skin of the patient's body and into the depth of the bodily tissue. The tissue piercing tip 129 of the stylet 127 will produce a guide tract of the combined structure direct the towards a target volume so that the tip 129 can be positioned to end at a desired target position in the bodily tissue. Then, when the stylet 127 is removed from the cannula 101, and the electrode 140 is inserted into the cannula 101, the extended portion 164 of the shaft of the electrode 140 will pass along the tract established by the stylet, and because the electrode and the stylet have the same shaft length, then the electrode distal tip 149 will then be at the same target position as was achieved by the stylet distal tip 129. Functionally, the stylet which is a rigid tissue piercing structure therefore establishes a pathway through the bodily tissue, so that subsequently the insertion of the electrode through the cannula when the style has been removed, will be far easier to carry out and require far less mechanical pushing and manipulating forces on the electrode. This has the advantage that the sharpened rigid stylet can be utilized in an efficient and ergonomic manner to achieve positioning of the cannula in a desired direction within the tissue to form a tract to a target position, and therefore a simplified way of passing the electrode within the cannula to place the tip of the electrode at a desire to target volume and target position within the bodily tissue. Accordingly, the combined exposed conduct the tip 111 plus 164 can be positioned in a correct direction and position with respect to a target volume, such as a cancerous tumor, so that when the combine tip 111 plus 164 is electrified by the output signal of a high frequency generator, then they thermal tissue ablation can be achieved in the tissue near the combined tip. The embodiment of FIG. 1A and FIG. 1B can comprise more than one cannula represented by 101, and each of the different cannulas can have different lengths different lengths D, and different tip exposed lengths U, so that different degrees of combined tip exposures 111 plus 164 can be achieved to accommodate clinical needs, as for example, the size of the target volume to be ablated, and also to accommodate a desired depth of penetration of the cannula shaft into the bodily tissue beyond the level of the patient's skin to reach the appropriate internal target volume, such as for example a cancerous tumor within the depths of the bodily tissue.

Figure 2:
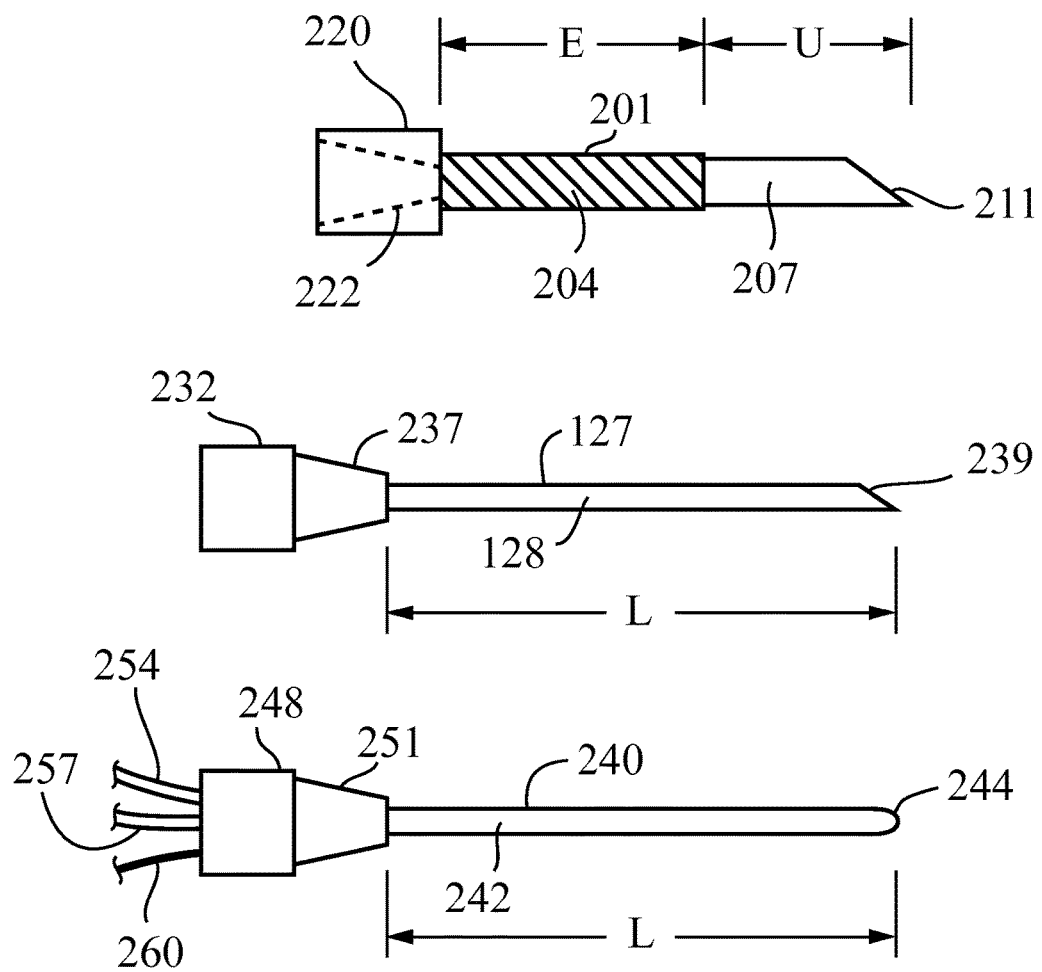
FIG. 2 is a schematic diagram in side elevation view showing a system of a cannula that is partially insulated and has been exposed distal tip, a stylet and/or needle that can be inserted into the cannula, and a cooled uninsulated high-frequency electrode that can also be inserted into the cannula wherein the stylet and the electrode have substantially the same length.

Referring to FIG. 2, an example of an embodiment of the present invention is shown in schematic and side elevation views. A cannula 201 has a shaft with an insulated portion 204, indicated by the hatched area, having length E, and with an un-insulated distal portion 207 of length U. The cannula has a distal tip 211 which has a sharpened point configuration. The cannula has a hub to 220 which has a female luer tapered internal diameter which can act as an engagement surface when the stylet or the electrode is inserted into the cannula. The stylet 127, in one example, comprises a rigid metal shaft 128 which has a length L and the rigid shaft can be an uninsulated metal shaft. In another example, the cannula shaft 128 can be a plastic shaft with a sharpened tip. The stylet has a hub 232 that has a male luer tapered surface 237 for engagement with the cannula's female Luer hub surface 222 when the stylet is inserted into the cannula. The stylet distal tip 239 has a sharpened beveled shape so that when the stylet is inserted into the cannula 201, the beveled tip of the stylet matches the beveled sharpened shape 211 of the cannula. Therefore, in the initial insertion process into the bodily tissue, the stylet that can be inserted into the cannula so that the hub of the stylet let and the hub of the cannula are engaged together, and their combined distal tip has the configuration of a sharp tissue piercing end which is adapted for piercing and penetrating the patient's skin and the patient's bodily tissue as the combined structure is manipulated by the clinician in the appropriate direction and with the appropriate depth so that the distal exposed tip 211 can be positioned within a desired target volume, such as a volume that is to be thermally ablated when the electrode is connected to the output signal of a generator. In one example, the distal end 239 of the stylet 127 does not extend substantially beyond the distal end 211 of the cannula 201, when the stylet 127 is engaged in the cannula 201. In one example, the distal end 239 of the stylet 127 extends only slightly beyond the distal end 211 of the cannula 201, when the stylet 127 is engaged in the cannula 201. In one example, the cannula 201 can have a closed distal end 211. In other examples, different types of engagement surfaces can be designed in the hub of the cannula, the hub of the electrode, and or stylet that are different from the Luer taper. These can involve mating surfaces, locking or twist locking devices, and other common hubs found on needles and cannula in the medical industry. In one example the stylet 127 can be a solid stainless steel rigid metal shaft with a sharpened point 239. In another example the system of stylet system 127 can comprise a hollow stainless steel needle with, for example, an obturating stylet within it that closes the end 239 to make a flush sharpened tissue piercing tip. Another component of the electrode system in FIG. 2 is a high-frequency electrode 240 which comprises an electrode shaft 242, which has on its proximal end a hub 248 with a Luer engagement surface 251 that can engage with the Luer hub 222 of the cannula when the electrode is inserted into the cannula. The length of the electrode shaft 242 is designated as L, and this can be, in one example, essentially the same length L as the stylet system shaft 128. In one example, the distal end 244 of the electrode 240 does not extend substantially beyond the distal end 211 of the cannula 201, when the electrode 240 is engaged in the cannula 201. In one example, the distal end 244 of the electrode 240 extends only slightly beyond the distal end 211 of the cannula 201, when the electrode 240 is engaged in the cannula 201 In one example the electrode distal tip shape 244 can be a sharpened point that is adapted for tissue piercing. In another example the electrode distal tip shape 244 can be more of a conical or bullet shaped point which makes it adaptable to follow a tissue tract in the bodily tissue. In another example, the tip 244 can be a hemispherical smooth tip which is not tissue piercing. In one example, the electrode 240 has an electrical connection wire 260 that can connected to the output signal of a high-frequency generator, not shown in this FIG. 2. When the connection 260 is made to a generator, the output signal of the generator can be connected to the shaft 242. In one example the shaft 242 is uninsulated and electrically conductive over at least a portion of its shaft so that when inserted into the cannula 201, electrical contact is made between the electrodes 240 and the conductive exposed tip 207 of the cannula. Therefore when the cannula and the electrode are combined, the output signal of the generator can be connected to the exposed tip 207, so that when the combined cannula and electrode within the bodily tissue, tissue near the exposed tip 207 can be heated by the output signal to cause a thermal ablation zone around the tip 207. In one embodiment the electrode 240 is a non-cooled electrode. In another example, the electrode 240 can have an internal cooling channel through which a coolant fluid from an external cooling supply, not shown in FIG. 2, can flow through the internal channel in cool electrode 240. When the electrode 240 is inserted into the cannula 201, the exposed tip 207 of the cannula can also be cooled by thermal conduction between the cannula 201 and the electrode shaft 242. The example of FIG. 2 can also comprise a multiplicity of cannulas, each having different exposed tip lengths U of the exposed tip 207. In one example, the system can comprise a set of cannulas each having different values of exposed length U that can be predetermined and known so that the clinician can select the cannula with the appropriate exposed tip length that is desirable to ablate a tissue volume of known size. In one example, the multiplicity of cannulas can be used with a single stylet such as 127 and with a single high-frequency electrode such as 240. One advantage of the system presented in FIG. 2 is that a set of cannulae with differing tip exposures U can be created for a given electrode and stylet, both of length L, by putting varying lengths of insulation E on multiple cannula shafts of with the same length E+U. Another advantage of the system presented in FIG. 2 is that a rigid cannula 201, once inserted into bodily tissue, creates a fixed channel within the tissue into which the stylet 127 and electrode 240 can be interchanged. Another advantage of the system presented in FIG. 2 is that, if the stylet 127 and electrode 240 do not extend substantially beyond the end of the cannula when they are each engaged in the cannula, interchange of the stylet 127 and electrode 240 within the cannula 201 placed in bodily tissue does not substantially change the extent of the assembly that contacts the tissue.

Referring to FIG. 3, another embodiment of the present invention is shown in side elevation view of its assembled components. In the upper of portion of the FIG. 3, embodiments of the system similar to that of FIG. 1A is shown in which the cannula 301 is completely insulated with insulation 304, indicated by the hatched area, and therefore the length of the cannula D is equal to the length of the insulated portion E as designated in FIG. 1A. A stylet system 307 is inserted into the cannula 301 so that the electrode hub 322 is engaged with the cannula hub 320 by means of a Luer taper surface 327. When that engagement of hubs is made, the distal portion 312 of the stylet 307 extends beyond the distal end 312 of the cannula 301 by a distance T. The distal stylet portion 307 that extends beyond the cannula distal end 314 can be a rigid tissue piercing structure with a sharpened tissue piercing and penetrating distal tip 310. In one example, the stylet structure can be a rigid metal tubular structure such as a sharpened needle. In another example, the stylet can be a solid structure such as a solid metal steel rod with a pointed tip or it can be a rigid firm plastic rod with a pointed tip. In one example, the distal tip 310 can be a needle like level, for example, a beveled shape point, or a tri-cut beveled tip. In another example, the tip 310 can be a trocar point or other pointed structure such as a sharpened conical structure. In one example, the designation of the overall length of the stylet structure as shown in FIG. 3 can be specified as LL. In the lower portion of FIG. 3, the same cannula 301 is shown with a high-frequency electrode 342 inserted into it, so that the electrode hub 348 engages with the cannula hub 320 by means of a Luer taper 351. In one example, the distal portion 347 of the electrode shaft 342 extends beyond the distal tip 314 of the cannula 301 by the distance T. This electrode extension distance can be, in one example, essentially the same as the stylet system extension distance shown in the upper FIG. 3 in the situation where the stylet is inserted into the cannula. In one example, the electrode extension portion 347 can be uninsulated so that when the electrode is connected to a high-frequency generator by connection wire 360, the output signal of the generator can be connected to and energize the exposed distal surface 347. In that case, when the combination of the cannula and the electrode is inserted into the bodily tissue, the output signal from the generator that is connected through the distal tip 347 to the surrounding bodily tissue can cause the heating and ablation of the tissue around the exposed distal electrode end 347. In one example, the shape of the electrode distal tip 344 can be a smooth rounded shape not adapted for tissue piercing, but adapted to follow a tract in the tissue made before hand by the tissue piercing stylet structure 312 and 310 shown in the upper figure in FIG. 3. In another example, the electrode distal tip can have a bullet shaped or conical shaped configuration which can enable the electrode 347, when inserted into the cannula 301, after the stylet 307 has made a tissue penetrating tract in the tissue, to follow the tract made by the tissue piercing extension 312 of the stylet 307. As shown in FIG. 3, in one example, the length of the extension of the electrode 347 beyond the cannula distal end 314 can be specified as T, and this distance can be essentially the same as the distance of extension of the sharpened stylet distal end 312 beyond the cannula distal tip 314. In one example, the electrode length as shown in FIG. 3 from the electrode hub reference point to the distal tip of the hub can be specified as LL which is essentially equal to the length specified for the equivalent points of the stylet system in the upper figure of FIG. 3. In one example, the length of the electrode shaft 342 and the length of the hubs shaft 307 can be made so that the very distal portion of the electrode tip 344 extends beyond the cannula distal end 314 by the same amount as the very distal end of the point of the cannula 310. In another example, the length of the stylet shaft and the length of the electrode shaft can be adapted so that the very distal end 344 extends beyond the cannula distal end 314 by the distance that the base of the sharpened tip 311 extends beyond the cannula distal end 314. Typically, a sharpened point such as 310 of the stylet system is not very long compared to the length of the exposed extension tip, so that some small variability in the matching of the lengths LL for both the stylet shaft and the electrode shaft can take into account the definition of the tip and geometry 310 of the stylet and the tip and geometry 344 of the electrode. In one example, the essential equivalence of the lengths of these two shafts takes into account small variations of definition of the distal end of the cannula shaft point and the distal end of the electrode shaft. In one example, the cannula 301 can have distance markings along its shaft as indicated by the lines 317, 318, and 319 as shown in FIG. 3. In one example, these lines can be centimeter markings so that each centimeter marking corresponds to a distance between the distal face 325 of the hub 320 and the cannula distal tip 310 of the stylet structure when inserted into the cannula, or between the cannula hub distal face 325 and the distal end of the electrode 344 when the electrode is inserted into the cannula. In another example, each line can correspond to the distance from the distal end of the electrode and/or stylet to the marker position when the electrode and/or stylet is respectively engaged in the cannula. These markings can, for example, correspond to a measure of the distance along the length corresponding to D plus T. This can help the clinician determine, in this situation, when the combination of the cannula plus the stylet or the combination of the cannula plus electrode has been inserted into bodily tissue. By observing which marker coincides with the patient's skin, the clinician can then infer or calculate the remaining distance along the total shaft distance D plus T. corresponding to the tip of the extension of stylet or the cannula. This can help clinician gauge and calculate the total depth of penetration from the skin surface to the distal end of the electrode, and this can assist in confirming that the distal end of the electrode is properly placed in a desired target position, such as in a cancerous tumor, deep within the body. If a desired target position for example is known to be at a certain depth of penetration beyond the patient's skin and in a given direction, the presence of these distance markings on the cannula shaft can confirm that the electrode tip is at the proper depth of penetration. Such distance markings, can in one example, the permanent ink markings on the insulation 304. In another example the distance markings can be black etched lines on the stainless steel tubing that makes up the shaft of cannula 301, and the insulation 304 can be sufficiently transparent that the markings can be visible through the insulation. In one example, the markings on the cannula can be in millimeters, or in centimeters, or in some fractional amount between these increments. Although such distance markings are not shown explicitly in the embodiments shown in FIGS. 1, 2, 4, 5, and 7, it is intended that these embodiments can also comprise such distance markings. In one example, an embodiment of the present invention can comprise a set of multiple cannulas, a stylet, and an electrode, and these can be can be constructed so that the distance D plus T corresponds to a known length such as, for example, 10 cm, 15 cm, 20 cm, 25 cm, 30 cm, 35 cm, 40 cm, 50 cm, 60 cm, 70 cm, 80 cm, 90 cm, 100 cm, or longer, or some other selected or known predetermined total shaft length corresponding to the distance from the cannula hub to the distal tip of the electrode beyond the cannula. The set of the multiple cannulas, single stylet, and single electrode having a specified value of D plus T, and each particular cannula has a specified length D to provide a specific tip extension length T. In one example, these specific extension lengths T for the different cannulas can be specific convenient lengths such as 1 cm, 2 cm, 2.5 cm, 3 cm, or 4 cm. In another example these extension length T. can be in the range of 5 to 10 cm, or longer. The clinician can then select one of the multiple cannulas so that the electrode extension length T can correspond closely to the desired length of ablation volume, which, for example, can be determined by the size of a cancerous tumor to be ablated. This has one advantage that the exposed tip lengths of the extension beyond the cannula tip is sufficient to ablate large tumors which can in many examples be greater than 1 cm in length, and other typical cases as great as 4 cm in length or in another clinical examples as large as 5, 6, 7, 8, 9, 10, centimeters or even greater in length. In one example, the cannula 301 can have a shaft which is made of a thin plastic tubing material having markings along its external surface corresponding to a determined millimeters or centimeter distances. In another example, the cannula can be a metal tubing which has etched millimeter and or centimeter distance markings On it, and the metal tubing can be insulated by a transparent or translucent dielectric insulating material such as a heat shrink Teflon tubing or some other heat shrink polymeric plastic tubing so that the millimeter and/or centimeter markings can be seen and visualized through the insulation coating.

Referring to FIG. 3, in one example, the cannula shaft 301, the stylet shaft 307, and the electrode shaft 347 can comprise etched, sandblasted, grooved, or otherwise interrupted surface markings that are visible on ultrasonic imaging that is carried out during the operators procedure when the cannula plus stylet and the cannula plus electrode has been inserted into the patient's body. In one example, the distal portion of the cannula shaft 301 can have a band of etched or interrupted surface markings around its circumference that can be visible under ultrasonic imaging. In one example, the last approximately 0.5 cm, or 1 cm, or other length portion of the distal end of the cannula shaft 301 can have an interrupted echogenic surface on its metal tubing. A thin plastic insulated coating above this interrupted surface will not degrade its visibility in ultrasonic imaging. Such an interrupted surface that is visible in ultrasound can be referred to as an echogenic or ultrasound visible marking. Variations of the pattern, position, or length of the ultrasonic visible markings can be made on the cannula, such as, for example, separated bands of ultrasonic visible markings spaced apart by a known distance. In another aspect, the stylet 307 can have on its distal portion echogenic markings such as bands of interrupted surfaces on its metal surface that are visible to ultrasound. In this way, when the combination of cannula with a stylet inserted is penetrated into the patient's tissue towards a target position, the clinician can apply in ultrasonic imaging device to the patient's skin and visualize real-time the echogenic markings on the cannula and/or the stylet which will provide the clinician with real-time visible imaging data related to the position of the tip of the stylet and/or the position of the distal end of the cannula relative to anatomical objects of interest. This provides the clinician way of confirming that the position of the cannula/stylet system has been placed in a desired position relative to a target volume such as a cancerous tumor volume, and also provides the clinician with the way of confirming that the ablation electrode is not too close to critical mobile structures nearby. Many biological target volumes, for example certain cancerous tumor volumes, are also visible on ultrasonic imaging. Therefore, an advantage of having echogenic markings on the components of the present invention is that it enhances the clinician's ability to confirm and to make real-time course corrections during the surgery to position the elements of the present invention at desired locations in the patient's body. In another aspect, the distal portion of the electrode 347 can have echogenic markings on its metal surface that are also visible to ultrasound imaging. In one example, a band of length approximately 5 mm, or 10 mm, or 15 mm, or some other length, of interrupted echogenic surface on the metal surface of tubing 342 can provide an echogenic surface detectable by intraoperative ultrasound imaging. In one advantage, having both the cannula and the electrode and the stylet having echogenic markings is that it will give the clinician an indication of the overall length of the tip extension of the electrode 347 beyond the cannula tip. The clinician then has a guide as to where the position of the heat ablation tip is located relative to his desired target volume. In another example, the cannula 301 does not have echogenic markings, and the electrode 342 can have an echogenic surface markings over its entire extended length beyond the tip of the cannula. In this example, as illustrated in FIG. 3, the electrode extending surface portion 347 is the conductive surface that will produce the ablation heating when it is electrified by the output signal of the generator. Therefore, being able to visualize that ablation tip real-time during the surgery provides the advantage that the clinician has knowledge before hand of where the ablation will take place relative to his selected targets. Another advantage of echogenic markings on the components of the present invention that are illustrated in the embodiments of FIGS. 1 through 7, is that the clinician can visualize the position of these components relative to normal anatomical objects as well as pathological objects near the path of the electrode system. In one example, the surgeon can desire to avoid a critical normal anatomical structure such as the intestine of the bowel, and having the ultrasonic real-time information on the position of the electrode relative to these delicate structures can be critical to avoid unwanted ablation of normal tissue. Another advantage is that it can allow the clinician more certainty in placing the electrode in the correct direction in the depth of the patient's tissue to adequately cover the target volume to be ablated. Another advantage is that when multiple electrodes are used in the same patient, for example for enlarging the ablation volume, the relative position of the multiple electrodes can be visualized real-time during the surgery and allow the clinician to make appropriate adjustments so that the spacing between the multiple ablating tips is appropriate to optimize the size of the ultimate ablation volume. Another advantage, is that by having the ultrasonic imaging information, as well as the imaging of surrounding anatomy and pathology using ultrasound, the surgeon can optimize the placement of one or more ablation electrode system relative to the anatomy according to a preplanned of this electrode positions which the clinician can have made based on pre-surgical imaging data for example from CT, MRI, ultrasonic imaging studies of the patient. This then would show up on ultrasonic imaging to give the clinician a location of the position of the ablative tip of the electrode in real-time during interrupted surgery. The use of ultrasonic imaging during interventional surgery is commonplace in modern operating theaters or procedure rooms. There exists already the practice of making echogenic markings on needles and cannula that are used for biopsy or other interventions. Ultrasound imaging is also used commonly to visualize pathologies such as tumors in the living body during surgery during diagnostics. The use of echogenic markings can similarly apply to the other embodiments of the present invention as illustrated and described herein related to the FIGS. 1 through 7. One advantage of using echogenic markings on the components of the present invention, including cannulas, stylet, and electrodes, is that it can give the clinician in real-time graphic imaging representation of the position of the conductive tip portions of the entire electrode system relative to the target volume which is to be ablated. Another advantage is that it allows the clinician to make real-time adjustments of the positions of the cannula, stylet, and/or electrode during the procedure relative to known anatomy, both pathological as well as normal anatomy, so as to navigate the direction, the depth, in the appropriate conductive tip exposures of these elements to optimally treat the desired target volume.

In one example, the cannula 301 can each have a variation in density at its distal end 314 so that its distal end 314 can be distinguished in x-ray, CT, or other radiographic images. In one example, the introducer stylet 307 can each have a variation in density at its distal end 310 so that its distal end 310 can be distinguished in x-ray, CT, or other radiographic images. In one example, the electrode 342 can each have a variation in density at its distal end 344 so that its distal end 344 can be distinguished in x-ray, CT, or other radiographic images. In one example, the cannula 301, the introducer stylet 307, and the electrode 342 can each have a variation in density at their respective distal ends 314, 310, and 344 so that each of these distal ends 314, 310, and 344 can be individually distinguished in x-ray, CT, or other radiographic images. One advantage of this design is that the extent of the tip length T can be visually identified in x-ray, CT, or other radiographic imaging. In one example, the variation in density can comprise a segment or band of a high density material. In one example, the variation in density can be a reduction in the thickness of the distal end of a structure. It is understood that the x-ray-visible markings can appear at other locations on the cannula 301, stylet 307, and electrode 342. It is understood that the x-ray-visible markings can have similar advantages to those of the echogenic markings described above.

In one example the electrode shaft, as illustrated in FIGS. 1 through 7, can be comprised of a rigid stainless steel tubing or other metal tubing. This has the advantage that the electrode shaft is robust against longitudinal or pushing force is which can be in encountered during insertion of the electrode through the cannula and on into bodily tissue beyond the end of the cannula.

Figure 4:
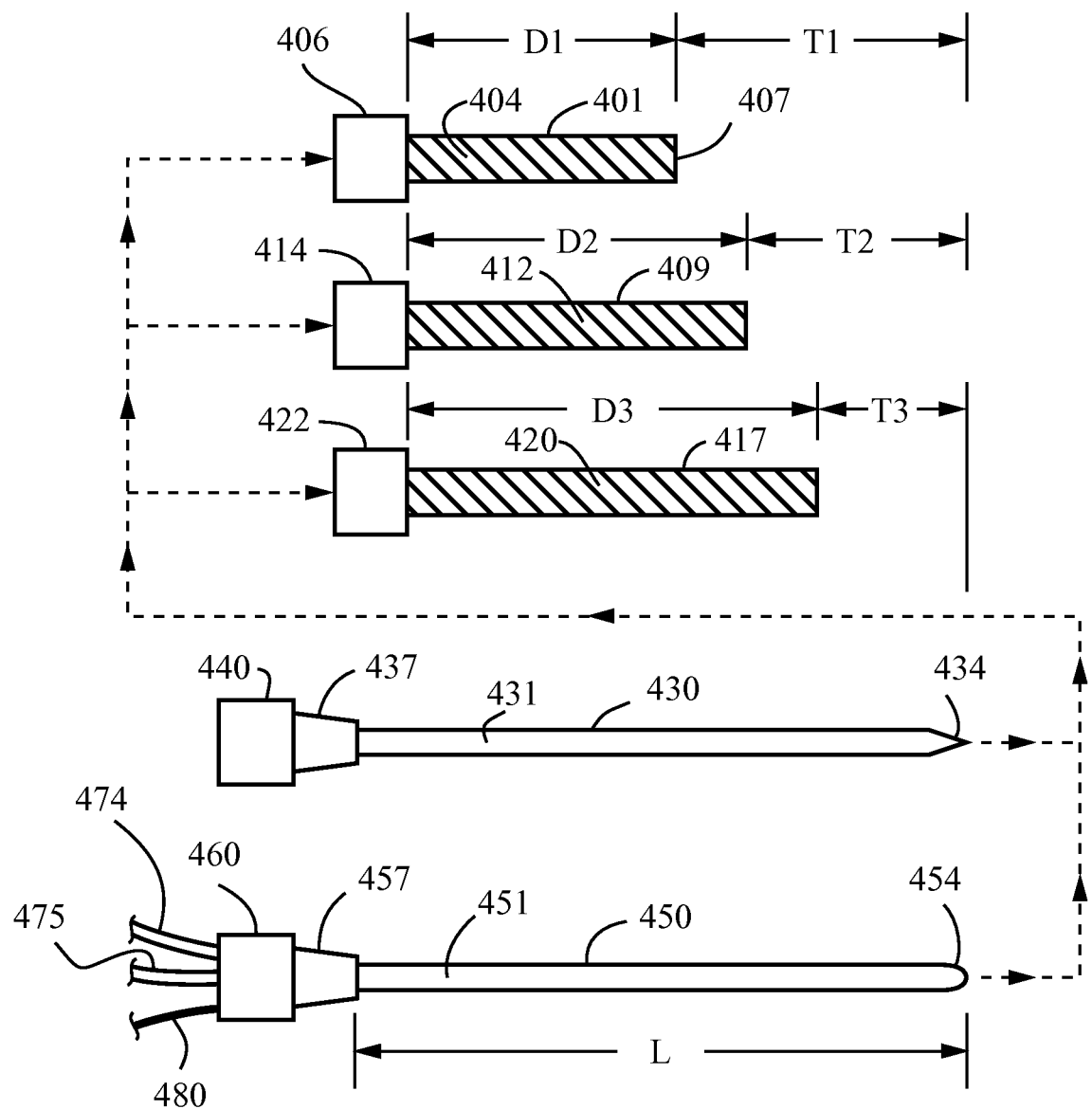
FIG. 4 is a schematic diagram in side elevation view showing a system of a multiplicity of cannulas that have shafts having a different shaft lengths, a stylet and/or needle with a tissue piercing point that can be inserted into any one of the cannulas, and the distal stylet extends a distance out of the distal end of any one of the cannulas by a known distance when the hubs of the cannula and stylet engage, and a cooled uninsulated high-frequency electrode that can also be inserted into any one of the cannulas and electrodes distal portion distal portion extends the same distance out of the distal end of any one of the cannulas as does the stylet when the hubs of the cannula and electrode engage.
Figure 5:
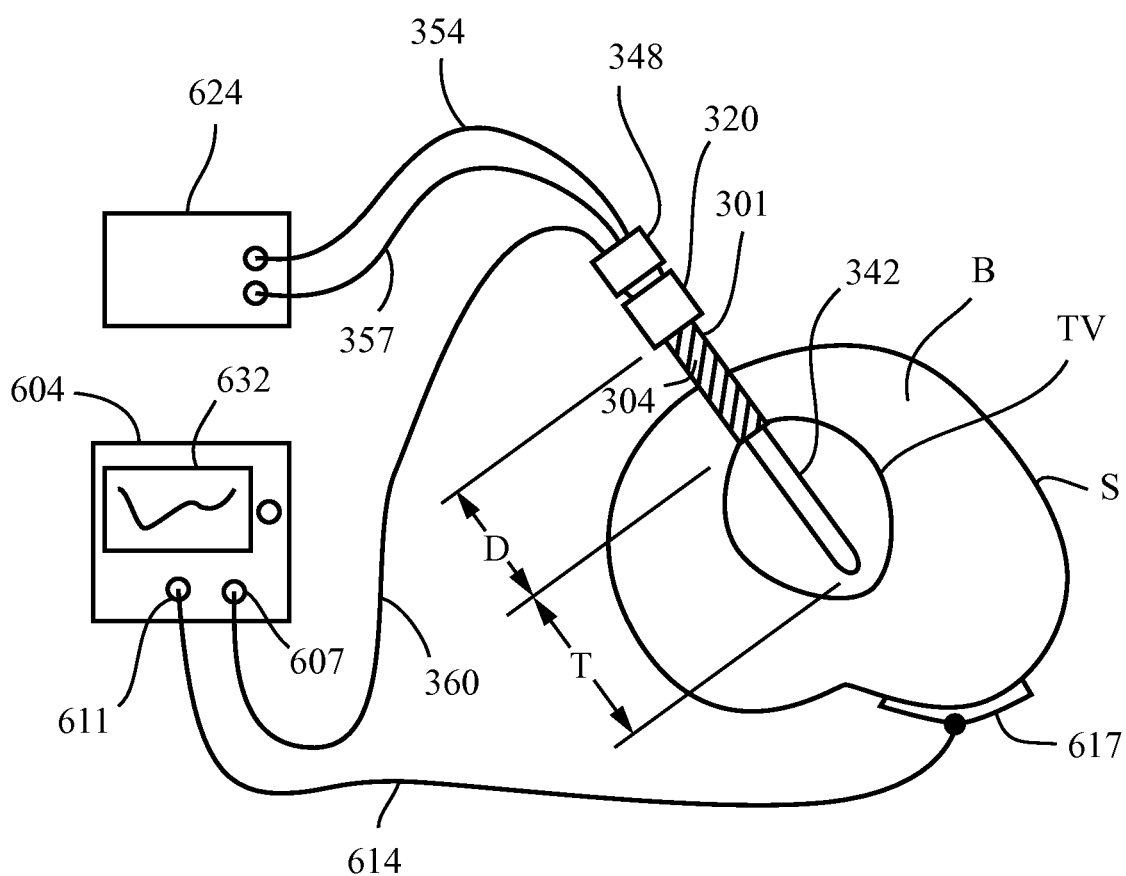
FIG. 5 is a schematic diagram showing placement of a high-frequency cooled electrode system into the tissue a patient's body so that the exposed tip extends into a target tissue, and a high frequency generator with graphic display of electrical parameters.

Referring to FIG. 4, the components of embodiments of the present invention are shown in schematic in side elevation view. The electrode system can comprise multiple cannulas represented in FIG. 4 by the examples of cannula 401, 409, and 417. These cannulas have different shaft lengths designated by D1, D2, and D3, respectively. Each of the shafts of the cannulas is essentially fully insulated, as represented by the hatched areas 404, 412, and 420, respectively. Each of the cannulas has a hub structure which is the same, represented by 406, 414, and 422, respectively. In one example, each of the cannulas can comprise a metal shaft with an insulated coating over. The metal shaft, in one example, can be a stainless steel hypodermic tubing, and the insulation can be of various types of materials such as, for example, Teflon, polyurethane, or other common insulating plastics. In another example, the cannula shaft can comprise a plastic tubing into which the stylet and/or the electrode can be passed. Another component in the system shown in FIG. 4 is the rigid stylet system 430 which has a rigid shaft portion 431, a hub 440 with engagement element 437, and a sharpened tissue piercing distal tip 434. As shown by the dashed lines with the arrows, the stylet 430 can be inserted into any one of the multiple cannulas 401, 409, and 417, so that when the stylet structure 440 engages with the respective hubs 406, 414, or 422, the distal tip will extend beyond the distal end of the cannulas, such as and 407 on cannula 401, by the distances T1, T2, and T3, respectively. The lengths D1, D2, and D3 for each of the cannulas 401, 409, and 417, respectively, can have predetermined and known values so that the respective tip extensions T1, T2, and T3 can also be known and predetermined. Therefore, with a set of multiple cannulas with such known length with respect to the length of the stylet system, the clinician can select an appropriate cannula so that the length of the cannula accommodates an appropriate and desired range of penetration of the cannula when the cannula plus stylet system is inserted into the tissue and directed to and proximate to a target volume to be ablated, and the degree of stylet tip extension beyond the cannula distal end is appropriate for producing a tract within the target volume along which tract the high-frequency electrode can subsequently follow preparatory to making a thermal ablation in the target volume. Also shown in FIG. 4 is a high-frequency electrode 450 which has shaft 451, a hub 460 with engagement surface 457, and distal end 454. The electrode is adapted to be inserted into each of the cannulas 401, 409, or 417 so that when electrode hub 460 engages with the respective hubs 406, 414, and 422, then the distal portion of the electrode 450 will extend beyond the distal end of the cannulas by the amounts T1, T2, and T3, respectively. In one example of a sequence of usage of these components, the composite of the stylet system inserted into a selected stylet is initially inserted percutaneously into the bodily tissue towards a target volume. Then, when the stylet system is removed from the cannula, and the high-frequency electrode is inserted into the cannula, the length extension of the electrode beyond the cannula distal end can be essentially the same as the length of extension of the stylet beyond the distal end of the cannula when the stylet system is engaged inside the cannula. The stylet system with is tissue piercing tip will have made a tract in the target tissue, so that when the electrode is subsequently inserted into the cannula after the stylet has been removed, and the electrode has an already established tract to follow through the target tissue along. This has one advantage that the electrode, in one example, does not have to have a tissue piercing distal tip since the stylet tract has already done the tissue piercing and established a pathway along which the electrode distal end can follow. The electrode system shown in FIG. 4, in one example, can be made in different embodiments in which they cannulas shaft lengths D1, D2, and D3 and the length L of the stylet system 430 and/or the electrode system 450 can have a selected and/or known and/or predetermined lengths to accommodate different depths of penetration towards a target volume and different lengths of exposed tip extension of the electrode beyond the cannula distal end to accommodate different volumes of thermal ablation to be made. For example, the overall length L of the stylet and/or electrode can be determined so that the hub to tip distance D plus T, or in the case of a specific cannula D1 plus T1, can be a length of 10, 15, 20, 25, or 30 cm which provides a range of depth of penetration that can accommodate the skin to target depth for most target volumes within the body. For each of these lengths D plus T, a set of, for example, four cannula can be supplied each having the appropriate length so that T1 equals 4 cm, T2 equals 3 cm, T3 equals 2 cm and T4 equals 1 cm. In this example, once the overall length D plus T has been selected, the surgeon can now select from a set of corresponding cannulas the appropriate cannula so that the exposed tip length of the ablation electrode can be selected as 1, 2, 3, or 4 centimeters Referring to FIG. 5, a schematic representation is shown of an arrangement of an electrode system, a high-frequency generator, and a coolant system that is adapted to be used to ablate a target volume within the living body. The living body is represented by the object B, the skin is represented by object S, and a target volume TV is shown within the living body which can be, for example, a tumor that is to be thermally ablated. An electrode system in accordance with the present invention is shown inserted percutaneously into the body. The electrode system comprises a cannula 301 that is, in one example, insulated over a portion of its surface, or in another example shown in FIG. 5, insulated over its entire surface as indicated by the hatched area 304. In the example shown in FIG. 5, the numbers correspond to the same numbers shown in the embodiment shown FIG. 3 above. In other examples, the configurations of FIG. 1, FIG. 2, and FIG. 4 could be substituted in this schematic drawing of FIG. 5. In one example, the cannula length D can be selected so that the distal end of the cannula just reaches the outer perimeter of the target volume TV, as illustrated schematically in FIG. 5. In an initial insertion step not shown in FIG. 5, a rigid stylet such a stylet 307 in FIG. 3 can be inserted into the cannula during the step that the cannula is inserted percutaneously through the skin S and on into the target volume TV. The stylet can then be removed and the electrode 342 can be inserted into the cannula 301, and the distal uninsulated portion of the electrode 342 extends beyond the distal end of the cannula by the distance T The length of the cannula D and the relative length of the electrode 342 can be preselected and known so that the extension distance T accommodates the dimension of the target volume TV to be ablated. In an alternative embodiment of the system shown in FIG. 5, multiple electrodes systems can be inserted into the target volume TV to produce an adequate length and lateral dimension of the ablation volume to cover the desired target volume TV, which, for example, can be a cancerous tumor to be destroyed. Illustrations of use of multiple electrodes systems for ablation are shown in the references cited in the BACKGROUND section above. Connected to the hub 348 of the electrode 342 is a connection wire 360 that plugs into the output jack 607 of high frequency generator 604, and this connects the output signal of the generator 604 which is active on the output Jack 607 to be connected to the uninsulated extension portion 342 of the electrode. Another output Jack 611 on the generator 604 has a wire 614 that connects the output of the generator to a reference electrode 617 that is attached to the patient's skin S. Therefore the signal output of the generator 604 that is generated across the output jacks 607 and 611 will cause high-frequency current to flow between the uninsulated electrode tip 342 and the surface area reference electrode 617. The high-frequency current passing through the tissue of the body B, as described in the cited references in the BACKGROUND section above, this will cause heating of the tissue near and around the exposed electrode tip 342. Various forms of the reference electrode 617 are known, and they can include conductive metal plates, commercially available electrical grounding pads used commonly in electrode surgery and high-frequency applications. In another example of a bipolar lesioning situation, a second electrode can be placed into the target volume; then, each of the electrodes can be connected to output jacks 607 and 611 so that the signal output of the generator 604, such as RF voltage, is now impressed between the exposed tip so the two electrodes within the bodily tissue. Description of bipolar high-frequency heating of tissue between bipolar electrodes is described in the references cited in the BACKGROUND section above. The high-frequency generator 604 can comprise a source of high power high frequency output signal, controls and switching systems that regulate the level of output delivered to one or more electrodes as the ablation process proceeds, and a graphics screen to display such as the display 632 which can monitor electrical parameters associated with the output signal and the electrodes such as RF current, power, voltage, and tissue impedance between the electrode and/or electrodes and the reference electrode 617. Examples of graphics displays, control systems, bipolar heating, and other control aspects of a high-frequency generator are referred to in the cited references in the BACKGROUND section above. Also shown in FIG. 5 are fluid coupling connections 354 and 357 which connect to the electrode hub 348 on one end, and connect on the other end to a cooled source 624. The cooled source 624 can comprise, in one example, a reservoir of cooled fluid such as chilled saline, a pump system to pump the cooled fluid into the input tube 354, which passes through an internal cooling channel in the electrode 342, and exits by the exit channel tube 357 to return to the coolant 624. Examples of cooled systems are given in the cited references in the BACKGROUND section above. In one example, coolant fluid is pumped through the electrode system as shown in FIG. 5, the same time that the output signal of the generator 604 is connected to the electrode tip 342. This cooled electrode system can produce larger ablation volumes than non-cooled electrodes, and it is useful in the field of interventional radiology for percutaneous minimal invasive ablative destruction of cancerous tumors.

Referring to FIG. 6, a process is described according to the present invention for ablating a tissue volume near a target position in the bodily tissue, for example, a cancerous tumor or other diseased volume within an organ or within the tissue of the living body. In one example, the embodiment of a system and apparatus described herein in FIGS. 1 through 5 and FIG. 7 can be used to implement the method described in FIG. 6. In step 601, the clinician can select the cannula and a stylet each having appropriate length so that when said stylet is inserted into said cannula so that the stylet hub engages the cannula hub, then the combined system can have been appropriate length to approach a desired target volume and provide sufficient extension of the stylet distal end beyond the cannula distal end to span an appropriate length along the target volume. Throughout this description of the present invention, the stylet can comprise a variety of structures, including a rigid stainless steel rod with a pointed tip, or a needle structure which includes a pointed tubular needle, which for example can be built from stainless steel tubing, together with an obturating needle stylet which when inserted into the needle closes the open end of the needle and provides an adequate pointed tip to the composite needle structure. In one example, a set of cannulas can be provided with different cannula shaft lengths which the clinician can select from, and also a stylet with a length selectable by the clinician so that when the stylet is inserted into a selected cannula, the distal end of the stylet will extend beyond the distal end of the cannula by a known amount. In step 601, in one example, the clinician can choose a stylet of appropriate length at the beginning of the process so that when the stylet is inserted into the cannula, and the composite cannula and stylet are inserted into the bodily tissue, then the composite length of the cannula and stylet will be sufficient to reach the deepest portion of a selected target volume. In step 601, in one example, the clinician can choose the appropriate length of the cannula, after having chosen a desired stylet length, so that the distal end of the cannula will be near to the shallowest portion of the target volume and so that the portion of the stylet that extends beyond the distal cannula tip adequately covers the length of the target volume along the direction in which the combined cannula and stylet is aimed into the target volume. In one example, step 601 can comprise selecting an appropriate geometry of cannula and stylet structure as illustrated in the embodiments of FIGS. 1 through 7 herein. In one example related to step 601, a cannula and stylet system as shown in FIGS. 1A and 1B can be chosen so that the combined uninsulated distal end of the composite cannula and stylet, designated as U plus T in FIG. 1A and FIG. 1B, corresponds to an appropriate the length of the ablation volume along the cannula and stylet direction. In another example related to step 601, a system is illustrated in FIG. 2 can be chosen by the clinician so that the overall length of the cannula, E plus U, is appropriate for the anticipated depth of penetration beyond the skin surface to the target position, and the exposed tip length U can be chosen to be appropriate for the length of the ablation volume to be made within the target volume. In another example related to step 601, the system of FIG. 3 can be chosen in the composite shaft length, D plus T as designated in FIG. 3, is appropriate to achieve a desired position of the stylet distal end within the target volume, and the cannula length D can be chosen so that the distal end of the cannula 314 is approximately at the tip of the nearest part of the target tissue volume, and the exposed tip T corresponds to the approximate length of the target tissue volume to be ablated along the direction of the insertion tract. In the example of FIG. 4 related to step 601, the clinician can choose from a multiplicity of cannulas such as 401, 409, and 417 to achieve the desired tip extension of the stylet, and therefore the tip extension of the electrode, beyond the distal end of the cannula when the combine stylet and the cannula are inserted into the tissue.

Referring to FIG. 6, in step 604 the combination of the stylet within the cannula, and in one example, with the engagement of their respective hubs to each other as described in FIGS. 1 through 4 above, is inserted into the bodily tissue so that the distal portion of the cannula and the distal tip of the stylet are positioned in desired locations in or near a target volume in the tissue. In one example for illustration, using a cannula and stylet system as shown in FIG. 3 and FIG. 4, step 604 can comprise the step of positioning the distal end of the stylet at approximately the deepest position of the ablation volume that is desired within the target volume, and the distal portion of the insulated portion of the cannula can be positioned approximately at the shallowest position relative the ablation volume that is desired. In that example, the extension portion of the stylet 307 beyond the cannula distal end 314 can approximately span the length of the target volume along the shaft direction. In another example, in which the cannula and/or stylet has distance markings on it, as for example in the embodiment of FIG. 3, the clinician can observe which distance marker is at the surface of the patient's skin when the cannula plus stylet system is inserted into the body, and by knowing the overall length D plus T, can calculate the depth relative to the skin of the distal end of the stylet within the bodily tissue. This depth can have been predetermined by image and data prior to or during the time of surgery, as for example using CT, MRI, or Ultrasound image data. Therefore, the markings on the cannula and/or cannula and stylet can be a visual indicator to the clinician of how deep the cannula and the distal tip of the stylet is within the body. The clinician commonly has done image and data of the patient prior to surgery, and can therefore have predicted the appropriate depth below the skin of the limits of the target volume. Therefore this knowledge of the depth of the cannula and the extended stylet tip can help guide the direction of the intervention. Similar illustrations can be made for the embodiments shown in the other figures herein described.

Referring to FIG. 6, in step 607 the stylet can be removed from the cannula and the high-frequency electrode can be inserted into the cannula. In one example, the electrode can have an uninsulated distal portion a portion which, when the hub of the electrode and the hub of the cannula are engaged, extends beyond the distal end of the cannula by the same distance that the distal end of the stylet extends beyond the distal into the cannula when the stylet is inserted into the cannula. In one example therefore, the depth measurements and positioning which were established by the clinician in step 601 and 604, correspond to equivalent depth measurements in positions of the extended electrode tip as for when previously the stylet was inserted into the cannula. In one example, the electrode can be a non-cooled electrode, for example, not having an internal coolant passing within it to cool the distal exposed extended tip of the electrode and cannula. In another example, the electrode can have an internal cooling channel and input and output ports near its hub to enable flow of a coolant fluid through the electrode, as described previously herein and in the references, so as to cool the distal uninsulated portion of the electrode that extends beyond the distal end of the cannula. In another example such as illustrated by the embodiments of FIGS. 1A, 1B, and 2, the cooling of the electrode can result in cooling of the distal exposed portion of the cannula through which the electrode passes. This can enable cooling of the uninsulated portion of the cannula that contributes to the energizing of surrounding tissue with the output signal of a high-frequency generator so as to heat the surrounding tissue.

Referring to FIG. 6, step 612 comprises connecting the electrode to a high-frequency generator so that output signal of the generator is connected to the electrode. In one example the electrode shaft can be completely uninsulated, so that it makes electrical contact with the cannula, and also so that the distal portion of the electrode that extends beyond the distal end of the cannula is uninsulated and makes electrical contact with surrounding tissue for the purpose of heating the tissue. In one example, the cannula can comprise a metal conductive tubing which has an uninsulated portion on this distal end, and therefore connecting the electrode to the output signal can also connect the output signal to the exposed portion of the cannula, which in turn makes electrical contact with the surrounding tissue to heat the tissue. Step 612 can also comprise, in the example where the electrode has an internal cooling channel with input and output ports connected to the channel for flowing a cooling fluid through the electrode, connecting the input and output ports on the electrode to a source of coolant fluid, so that when the cooling fluid flowing, the distal portion of the electrode that extends beyond the cannula distal end is cooled, and in the case that the cannula has an exposed portion, then exposed cannula portion can also be cooled.

Referring to FIG. 6, step 616 comprises applying the output signal from the generator to the electrode to cause a high-frequency current to flow through the electrode to the tissue that surrounds the uninsulated portion of the electrode that extends beyond the distal end of the cannula, and in the case that the cannula has an uninsulated portion, high-frequency current will also flow through the electrode to the cannula, and consequently to the tissue surrounding the uninsulated portion of the cannula. In the case that the electrode is adapted for fluid cooling, the uninsulated portion of the electrode, and the uninsulated portion of the cannula, is cooled when the output signal of the generator is connected to the electrode. The cooling of the electrode and cannula exposed portions can alter the heating distribution of the tissue around the electrode and cannula, in one example can increase the size of the ablation volume of the tissue surrounding the electrode and cannula tips. In one example, feedback control of the output signal can be used to regulate the heating of the bodily tissue. In one example, manual control of the output signal can be used to regulate the heating of the bodily tissue. In one example, a temperature measured at or near the electrode tip can be used to regulate the output signal. In one example, an impedance of the measured between two output jacks of an high frequency generator can be used to regulate the output signal. In one example, electrical output measurements, such as Voltage, Current, Power, can be used to regulate the output signal.

Figure 7:
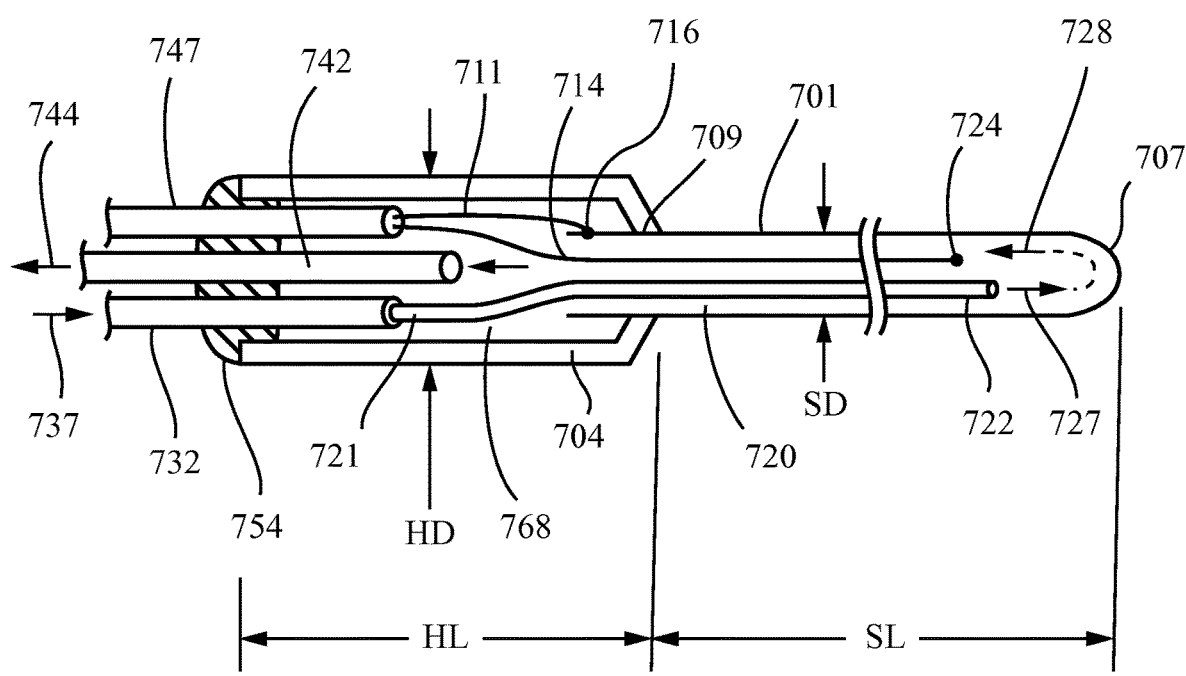
FIG. 7 is a schematic diagram in sectional side elevation view showing the internal fluid pathway and fluid channels through the hub in the shaft of a high-frequency electrode for compact and high efficiency fluid coolant flow.

Referring to FIG. 7, a side elevation view in partial sectional view is shown of one embodiment of the present invention showing aspects of the internal cooling system and electrical and thermal connections. Electrode shaft 701 can comprise, in one example, a rigid stainless steel tubing. In one example, a rigid stainless steel tube is main structural element of the electrode shaft 701, providing stiffness and rigidity to the electrode shaft 701. In one example, the electrode distal shaft can have a distal tip 707 that has a non-tissue piercing shape such as a rounded or elliptically shaped contour. In another example, distal tip 707 can be a tissue piercing point having a sharpened tip such as a trocar or a beveled needlelike tip. In another example, the electrode shaft 701 can comprise a catheter type structure which has a portion of its external surface that is electrically conductive. In one example, the electrode shaft can comprise a catheter made of a plastic material that can have on its external surface a metalized coating or a conductive wire helix or mesh outside layer so that its external surface is a substantially exposed electrically conductive surface. At the proximal end of a metal shaft 701, in one example the shaft is connected to a hub 704 at the junction 709. The junction 709 can be, for example, a glued joint that can be mechanically robust and also be sealed to fluid pressure to prevent leaks of a coolant fluid within the electrode. In one example, the hub 704 can be constructive of a plastic insulating material. In another example, the hub 704 can be made of a metal or other rigid material. In one example, and electrical conductor 711 connects the output signal from the high-frequency generator by the electrical junction 716 to the conductive portion of the electrode shaft 701. In one example, the conductor 711 can be an electrical wire. Also shown is electrical connection 714 which can carry temperature sensing information from a temperature sensor 724 inside the shaft 701 of the electrode. In one example, element 714 can comprise thermocouple wires, for example copper and constantan wires, which connect electrically at 724 to form a thermocouple junction at position 724. In another example, 714 can comprise a stainless steel tubing inside of which are thermocouple wire elements that connect to a thermocouple junction 724. In one example, 714 can be a thin stainless steel tubing inside of which is a constantan wire that is electrically connected to the stainless steel tubing near 724 to provide a stainless steel to constantan thermocouple junction which provides temperature sensing information at the distal location 724. In another example, 714 can be a stainless steel tubing inside of which is a constantan wire and a copper wire which are electrically connected at the distal portion of the tubing 724 to provide temperature sensing information at the position 724. In one example, the high-frequency or RF carrying wire elements represented by 711 can be part of the element 714. The electrical connection of the output signal from the high-frequency or RF generator can be made to a thin stainless steel tubing that is part of 714, and the electrical connection of the output signal to the exterior stainless steel conductive tubing 701 can be made by means of contact of element 714 to the inside of the stainless steel tubing 701. In that example, the electrical connection of 711 to the conductive tubing 701 by the junction 716 can be eliminated. In one example, multiple temperature-sensing elements, like 724, can be incorporated into the electrode at multiple locations. In one example, the output signal carrying elements and the temperature sensing elements, exemplary embodiments of which have been described herein in the references, can be carried back out of the hub by conduit 747. In one example, conduit 747 can be flexible plastic tubing and can be connected to the output jacks of a high-frequency generator by means of connection junctions and/or extension cables, which are not shown explicitly in FIG. 7 and examples of which are shown in the embodiments in the references cited in the BACKGROUND section herein. The output generator can be adapted to measure of the temperature signal at the temperature sensor 724 as well as to supply signal output to the electrode out of shaft 701. Also shown in FIG. 7, a fluid flow path and input and output connections can provide coolant flow within the electrode 701 in order to cool the electrode during application of RF or high frequency output signal from an RF generator. An inflow tubing line 732 carries coolant fluid into the electrode, illustrated by arrow 737. In one example, input tubing 732 connects to an internal inflow tubing 721, which is contained within the electrodes 701 and runs along the interior of the of the electrode shaft 701, and which carries coolant fluid to the distal end of the electrode. The distal end 722 of the tubing 721 can be an opening in the tubing which enables coolant fluid that is pumped in through 732 to exit into the inner space of the electrode shaft tubing 701 near the distal end 707 as illustrated by the arrow 727 and 728. The fluid exits the tubing 722 circulates back as illustrated by arrows 727 and 728 and flows backwards through the interior lumen 720 of tubing 701, and then flows into the exit tube 742 to exit the hub as illustrated by arrow 744. In one example, the external connection 732 can be a plastic tubing, and the inner inflow tubing 721 can be a metal tubing such as a stainless steel hypodermic tubing. The proximal end of the hub 714 can be fluid sealed by a sealant illustrated by the hatched area 754. In one example, sealant 754 can comprise an epoxy seal in which, and in one example, the epoxy can be injected around the tubing's 732, 742, and 747 as well as the proximal end of the hub 704 itself so that any fluid under pressure in the inner space 768 of hub 714 will be sealed against any escape path out of the proximal end of the hub. In one example, the hub 704 and it's distal end is fluid sealed to the electrode shaft 701 at the junction 709 so that coolant fluid under pressure within the inner space 720 of the electrode shaft tubing and the inner space 768 of the hub 704, will be sealed against fluid leaks.

Referring to FIG. 7, this embodiment has one advantage that the geometric arrangement of the tubing 732, 742, and 747 that connect to the hub 704 and to the internal shafts within the electrode shaft 701 can be made in a very compact and efficient form. In one example, the input tubing's 732, 742, and 747 can have outer diameters in the range of 1 to 2 mm. These can be joined to a hub 704 that has an outer diameter HD which, in one example, can be between 9 and 15 mm. In one example, the hub diameter can be approximately 10 mm. In another example, the hub diameter and be less 5 millimeters In another example, the hub diameter can be 3 mm. In another example, the hub diameter can be 4 mm. In another example, the hub diameter can be 5 mm. In another example, the hub diameter can be 6 mm. In another example, the hub diameter can be 7 mm. In another example, the hub diameter can be 8 mm. In another example, the hub diameter can be 9 mm. This small diameter electrode has one advantage that multiple such mechanically independent electrodes can be inserted into the body towards a target volume with the electrode shaft and hubs clustered close together. In one example, a set of multiple electrodes, as exemplified in the embodiments of FIGS. 1 through 7, can be inserted into the patient's body in a parallel clustered configuration with the electrode separation of approximately 10 mm. This has the advantage that using mechanically independent electrodes, a clustered set of cooled RF electrodes can be arranged in an internal target volume. In one example, as an illustration of this advantage, a tight cluster of several such electrodes can be inserted between the ribs to approach a target volume in the liver or in the lung. The small diameter of the hub can has one advantage that the multiple electrodes can be clustered in a close together arrangement to approach a deep target through the limited space between the patient's ribs. Because the compact construction of the hub, as exemplified by FIG. 7, in one example, a hub diameter HD of approximately 10 mm is achieved which is substantially smaller than previously implemented cooled RF electrodes as exemplified by the electrodes of Valley lab, Radionics, and Baylis referred to in the BACKGROUND section above. Another advantage of the configuration in FIG. 7 is that the length HL of the hub 704 can be made significantly shorter and lighter weight than the hubs of previous cooled RF electrode systems of Valley lab, Radionics, and Baylis, referred to in the BACKGROUND section. In one example, the length HL can be in the range of 0.5 to 1.5 inches. One advantage of smaller diameter HD and the shorter length HL of the design of FIG. 7, is that the hub can be light weight and unobtrusive. This has the advantage that there can be less torque applied to the shaft of 701 when the electrode is inserted into the patient's body, which reduces the chance of the electrode moving from its desired target position once electrode has been established in that target position.

Referring to FIG. 7, in another aspect, the arrangement of elements in this embodiment of the invention within the electrode shaft 701 enables a compact, simplified, and easily manufactured electrode. In one example electrode shaft 701 can have a rigid stainless steel tubing construction with the other diameter SD of the electrode shaft being in the range of 1 to 2 mm. In one example, the element 714 can comprise a thin metal stainless steel tubing having outer diameter between 0.1 and 0.5 mm, and can carry the RF signal by being connected electrically through cable 747 to the output of the RF generator. Inside of tubular element 714 can be a thermocouple element such as a constantan wire that enables the thermocouple junction to be positioned at the distal end 724. The internal inflow tubular element 721 can be a thin-walled stainless steel tubing with diameter in the range of 0.1 to 0.7 mm. One advantage is that the use of a single internal inflow tubing 721, with return fluid flow passing through the inner space 720 of the electrode shaft 701 enabling the fluid to pass into the hub chamber 768 and out the exit to 742, there is a very efficient low impedance fluid passageway of the coolant fluid unit out of the electrode shaft while maintaining a small diameter of the electrode shaft. In one example, the length of the shaft SL can range from 5 cm to 30 cm, or more. Electrodes of different shaft lengths can be made available so that the clinician can select the desired length on the application and on the depth of the target tissue within the body to be reached.

Referring to FIG. 7, in another example, the tube 744 can carry inflow of cooling fluid, and the tube 737 can carry outflow of cooling fluid.

In FIGS. 1 through 7, the shaft of the electrode can have a main structural element which provides rigidity and stiffness to the electrode shaft comprising a metal tubing that is part of the outer wall of the electrode shaft.

A number of embodiments of the invention have been described. Nevertheless, it will be understood that various modifications may be made without departing from the spirit and scope of the invention. Accordingly, other embodiments are within the scope of the following claims.

The invention claimed is:

1. An electrode system adapted for introduction into bodily tissue comprising:
at least two cannulas, each of the cannulas having a cannula distal end and a cannula proximal end, each of the cannulas having a cannula hub fixedly attached at the cannula proximal end without a set screw or a user-adjustable device, each of the cannulas having a cannula shaft having a lumen therethrough, and the cannula shaft having a cannula insulated portion of its external surface that is insulated;
a stylet having a stylet shaft with a stylet distal end and a stylet proximal end, the stylet having a stylet hub fixedly attached at the stylet proximal end without a set screw or a user-adjustable device; and
an electrode having an electrode shaft with an electrode distal end and an electrode proximal end, the electrode having an electrode hub fixedly attached at the electrode proximal end without a set screw or a user-adjustable device, the electrode shaft having at least in part an electrode uninsulated portion on its surface,
whereby when the stylet shaft is inserted into the cannula lumen of one of the at least two cannulas, said stylet hub engages with the cannula hub of the one of the at least two cannulas such that the stylet has a predetermined stylet length between the distal end of the stylet shaft and the point of engagement between the stylet hub and the cannula hub and the combination of the one of the at least two cannulas and said stylet is adapted to be inserted into the bodily tissue, and
when the electrode shaft is inserted into the cannula lumen of the one of the at least two cannulas with the stylet not inserted in the cannula lumen, said electrode hub engages with the cannula hub of the one of the at least two cannulas such that the electrode has a predetermined electrode length between the distal end of the electrode shaft and the point of engagement between the electrode hub and the cannula hub, at least a part of the electrode uninsulated portion is within said lumen of the one of the at least two cannulas, and the combination of the cannula shaft of one of the at least two cannulas and the electrode shaft form a combined exposed tip having an uninsulated external surface of said combination of shafts,
wherein the predetermined electrode length is substantially the same as the predetermined stylet length such that said electrode distal end is in substantially the same position relative to the cannula distal end of the one of the at least two cannulas as is said stylet distal end is relative to the cannula distal end of the one of the at least two cannulas;
wherein said electrode is adapted for connection to a high-frequency generator so that output signal from the high-frequency generator is connected to said electrode uninsulated portion, and when said electrode is inserted into any of the at least two cannula, said combined exposed tip is configured to deliver output signal from the high-frequency generator;
wherein said electrode has an internal fluid channel, a fluid input port and a fluid output port, the input port being adapted to be connected to a source of coolant fluid so that the coolant fluid can flow into the fluid input port, through the internal fluid channel, and out of the fluid output port, whereby said combined exposed tip is cooled by said coolant fluid when said electrode is inserted into any of the at least two cannulas; and
wherein when the electrode shaft is inserted into any of the at least two cannulas, each of the combination of electrode shaft and one of the at least two cannulas form a combined exposed tip of a different length.

2. The system of claim 1, wherein the length of said stylet shaft and said electrode shaft are substantially equal.

3. The system of claim 1, wherein said stylet shaft is a rigid tissue piercing shaft.

4. The system of claim 1, wherein said electrode shaft has a non-tissue piercing tip at said electrode distal end.

5. The system of claim 1, wherein said electrode shaft has a tissue piercing tip at said electrode distal end.

6. The system of claim 1, and further including a conductive wire adapted to connect said electrode to the output signal of the high-frequency generator.

7. The system of claim 1, wherein said stylet comprises a hollow needle with an obturating stylet that is adapted to be inserted into the needle.

8. The system of claim 1, wherein the hub of said electrode is 10 mm or less in width.

9. The system of claim 1, wherein substantially all of the external structural element of said electrode shaft comprises a rigid metal tube.

10. The system of claim 1, wherein each of said at least two cannulas, and/or stylet, and/or electrode comprises x-ray visible markings at known positions on their shafts so that when the combination of one of the at least two cannulas and said stylet, or the combination of one of the at least two cannulas and said electrode are inserted into the patient's body tissue, an x-ray, fluoroscopy, CT, or other radiographic imaging machine can be used to visualize the position of portions of the cannula, and/or said stylet, and/or said electrode relative to the structures in the patient's body.

11. The system of claim 1, wherein each of said at least two cannulas, and/or stylet, and/or electrode comprises ecogenic markings at known positions on their shafts so that when the combination of one of the at least two cannulas and said stylet, or the combination of one of the at least two cannulas and said electrode are inserted into the patient's body tissue, an ultrasonic imaging machine can be used to visualize the position of portions of the cannula, and/or said stylet, and/or said electrode relative to the structures in the patient's body.

12. The system of claim 1, wherein said stylet comprises a needle and a needle's stylet which have a sharpened tissue piercing point.

13. The system of claim 1, wherein said known length is greater than 6 mm.

14. The system of claim 1, wherein said predetermined electrode length is about 10 mm.

15. The system of claim 1, wherein said predetermined electrode length is about 20 mm.

16. The system of claim 1, wherein said predetermined electrode length is about 30 mm.

17. The system of claim 1, wherein said predetermined electrode length is about 40 mm.

18. The system of claim 1, wherein said predetermined electrode length is about 25 mm.

19. The system of claim 1, wherein said predetermined electrode length is about 50 mm.

20. The system of claim 1, wherein said predetermined electrode length is about 60 mm.

21. The system of claim 1, wherein said predetermined electrode length is greater than 60 mm.

22. The system of claim 1, wherein the surface of the electrode shaft is metal.

23. The electrode system of claim 1 wherein,
each of said cannula shafts has the cannula insulated portion and a cannula uninsulated portion, the cannula uninsulated portion comprises an uninsulated surface of the cannula shaft at the cannula distal end of known cannula tip length,
wherein each of the at least two cannulas uninsulated portion forms a part of the combined exposed tip, and said electrode and each cannula are adapted so that said electrode distal end cools the cannula uninsulated portion when said electrode is inserted into one of the at least two cannulas.

24. The system of claim 23, wherein said combination of said stylet and one of the at least two cannulas has a combined distal tip having a sharpened tissue piercing point.

25. The system of claim 23, wherein said known cannula tip length is about 10 mm.

26. The system of claim 23, wherein said known cannula tip length is about 20 mm.

27. The system of claim 23, wherein said known cannula tip length is about 30 mm.

28. The system of claim 23, wherein said known cannula tip length is about 40 mm.

29. The system of claim 23, wherein said known cannula tip length is about 25 mm.

30. The system of claim 23, wherein said known cannula tip length is about 50 mm.

31. The system of claim 23, wherein said known cannula tip length is about 60 mm.

32. The system of claim 23, wherein said known cannula tip length is greater than 60 mm.

33. The system of claim 23, wherein said predetermined electrode length and predetermined stylet length are a known length for each of said at least cannulas.

34. An electrode system adapted introduction into bodily tissue comprising:
at least two cannulas, each cannula having a cannula distal end and a cannula proximal end, the cannula having a cannula hub fixedly attached at the cannula proximal end, the cannula having a cannula shaft at the distal end, the cannula having a lumen therethrough, the cannula shaft being substantially insulated, the cannula having a predetermined cannula length; wherein the cannula lengths of the at least two cannulas are different from each other;
a tissue piercing needle having a needle shaft with a needle distal end and a needle proximal end, said needle having a shaft portion that is adapted to be inserted into the cannula lumen of any of the at least two cannulas the tissue piercing needle having a needle hub fixedly attached at a proximal end of the tissue piercing needle and having a sharpened tissue piercing point on a distal end of the tissue piercing needle, the needle having a predetermined electrode length between the distal end of the needle shaft and the part of the needle hub that is configured to engage with the cannula hub of any of the at least two cannulas;
an electrode having an electrode shaft with an electrode distal end and an electrode proximal end, said electrode having a shaft portion that is adapted to be inserted into the cannula lumen of any of the at least two cannulas, the electrode having an electrode hub fixedly attached at the electrode proximal end, the electrode having a predetermined electrode length between the distal end of the electrode shaft and the part of the electrode hub that is configured to engage with the cannula hub of any of the at least two cannulas;
wherein the electrode length and the needle length being substantially equal:
wherein the electrode hub and the cannula hub of any of the at least two cannulas are configured to engage with each other without a set screw or a user-adjustable device;
whereby when the needle shaft of said tissue piercing needle is inserted into the cannula lumen of one of the at least two cannulas such that said tissue piercing needle hub engages with the cannula hub of the one of the at least two cannulas without a set screw or a user adjustable device, the distal end of the tissue piercing needle extends beyond the cannula distal end of the one of the at least two cannulas by a predetermined and known length and the one of the at least two cannulas and said tissue piercing needle are adapted to be inserted together into the bodily tissue so that the distal end of the tissue piercing needle is located at a target position within said bodily tissue, and
whereby when the tissue piercing needle is removed from the cannula lumen of the one of the at least two cannulas and said electrode is inserted into the one of the cannula of the at least two cannulas, said electrode hub engages with the cannula hub of one of the at least two cannulas, the portion of the electrode shaft that extends beyond the cannula distal end is uninsulated, and the electrode distal end extends beyond the cannula distal end by the same length as said predetermined and known length of the tissue piercing needle so that said distal end of the electrode is directed along a same tract as said tissue piercing needle within the one of the at least two cannulas and is adapted to be located at the same target position within said bodily tissue;
wherein said electrode is adapted to be connected to a high-frequency generator so that said uninsulated portion of the electrode shaft that extends beyond the cannula distal end of any of the at least two cannulas is configured to output signal from the high-frequency generator;
wherein said electrode has an internal fluid channel, a fluid input port and a fluid output port the input port being adapted be connected a source of coolant fluid so that the coolant fluid can flow into the input port, through the internal fluid channel, and out of the output port, whereby said uninsulated portion of said electrode that extends beyond the cannula distal end any of the at least two cannulas is cooled by said coolant fluid; and wherein each of the at least two cannulas provides for a different length of said uninsulated portion of the electrode shaft that extends beyond the cannula distal end when the electrode shaft is inserted into each of the at least two cannulas.

35. The system of claim 34, wherein the length of said needle shaft and said electrode shaft are substantially equal.

36. The system of claim 34, wherein said needle shaft is a rigid tissue piercing shaft.

37. The system of claim 34, wherein said electrode shaft has a non-tissue piercing tip at said electrode distal end.

38. The system of claim 34, wherein said electrode shaft has a tissue piercing tip at said electrode distal end.

39. The system of claim 34, and further including a conductive wire adapted to connect said high-frequency electrode to the output signal of a high-frequency generator.

40. The system of claim 34, wherein said known length is greater than 6 mm.

41. The system of claim 34, wherein said predetermined and known length is about 10 mm.

42. The system of claim 34, wherein said predetermined and known length is about 20 mm.

43. The system of claim 34, wherein said predetermined and known length is about 30 mm.

44. The system of claim 34, wherein said predetermined and known length is about 40 mm.

45. The system of claim 34, wherein said predetermined and known length is about 50 mm.

46. The system of claim 34, wherein said predetermined and known length is about 60 mm.

47. The system of claim 34, wherein said predetermined and known length is greater than 60 mm.

48. The system of claim 34, wherein each of said at least two cannulas, and/or tissue-piercing needle and/or electrode comprises ecogenic markings at known positions on their shafts so that when the combination of one of the at least two cannulas and said tissue-piercing needle, or the combination of one of the at least two cannulas and said electrode are inserted into the patient's body tissue, an ultrasonic imaging machine can be used to visualize the position of portions of the cannula, and/or said tissue-piercing needle, and/or said electrode relative to the structures in the patient's body.

49. The system of claim 34, wherein each of said at least two cannulas, and/or tissue-piercing needle, and/or electrode comprises x-ray visible markings at known positions on their shafts so that when the combination of one of the at least two cannulas and said tissue-piercing needle, or the combination of one of the at least two cannulas and said electrode are inserted into the patient's body tissue, an x-ray, fluoroscopy, CT, or other radiographic imaging machine can be used to visualize the position of portions of the cannula, and/or said tissue-piercing needle, and/or said electrode relative to the structures in the patient's body.

50. The system of claim 34, wherein the diameter of said electrode hub is less than 10 mm.

51. The system of claim 34, wherein said length of extension is a known length for each of said at least two cannulas.

52. The system of claim 34, wherein substantially all of the outer portion of said electrode shaft comprises a rigid metal tubing.

53. The system of claim 34, wherein substantially all of said electrode shaft has an uninsulated conductive surface.

54. A system for heating of bodily tissue comprising:

at least two cannulas of different lengths, each cannula having a cannula distal end and a cannula proximal end, the cannula having a cannula hub fixedly attached at the cannula proximal end, said cannula having a cannula shaft having a lumen therethrough, and the cannula shaft being substantially insulated;

a tissue piercing needle having a needle shaft with a needle distal end and a needle proximal end, the needle having a needle hub fixedly attached at the needle proximal end and having a sharpened tissue piercing point on the needle distal end, the needle shaft having a predetermined needle length from the distal end of the needle hub to the distal end of the needle shaft, the tissue piercing needle configured to be inserted into the cannula lumen of any of the at least two cannulas, and the needle hub and the cannula hub being configured to engage with each other without a set screw or a user-adjustable device, so that when the tissue piercing needle is inserted into the cannula lumen of one of the at least two cannulas and said needle hub engages with the cannula hub of one of the at least two cannulas, the needle distal end extends beyond the cannula distal end by a known predetermined extension length of the one of the at least two cannulas, and said tissue piercing needle and the one of the at least two cannulas are inserted together into bodily tissue so that said distal end of said tissue piercing needle is adapted to be located at a target position in the bodily tissue;

a high-frequency electrode having an electrode shaft with an electrode distal end and an electrode proximal end, the high-frequency electrode having an electrode hub fixedly attached at a proximal end of the high-frequency electrode, the electrode shaft having a predetermined electrode length from the distal end of the electrode hub to the distal end of the electrode shaft, the electrode length being substantially equal to the predetermined needle length, the electrode shaft configured to be inserted into the cannula lumen of any of the at least two cannulas, and the electrode hub and the cannula hub being configured to engage with each other without a set screw or a user-adjustable device, so that when said electrode hub engages with the cannula hub of the one of the at least two cannulas, the portion of the electrode shaft that extends beyond the cannula distal end is uninsulated, and the uninsulated extension portion of the electrode shaft extends beyond the cannula distal end by the same known predetermined extension length for that cannula and is adapted to be located at the target position in the bodily tissue, wherein the distal end of said high-frequency electrode is directed along the tract that is the same as the tract of the tissue piercing needle when its hub was engaged with the cannula hub;

wherein said electrode further comprises an internal fluid channel, a fluid input port and a fluid output port; the input and output ports being adapted to be connected to a source of coolant fluid so that the coolant fluid can flow into the input port, through the internal fluid channel, and out of the output port, whereby said uninsulated portion of said electrode that extends beyond the cannula distal end is cooled by said coolant fluid;

a high-frequency generator adapted to produce an output signal, and for connection of the high-frequency generator to said high-frequency electrode, and said high-frequency electrode being adapted so that when connected to said high-frequency generator, said uninsulated extension portion of said high-frequency electrode is connected to said output signal and said output signal is adapted to cause heating of the bodily tissue near said uninsulated extension portion of said high-frequency electrode; and wherein the known predetermined extension length of the uninsulated extension portion of the electrode shaft is different for each of the at least two cannulas.

55. The system of claim 54, wherein substantially all of the length of said electrode shaft has a conductive uninsulated surface.

56. The system of claim 54, wherein each of the at least two cannulas, and/or tissue piercing needle, and/or electrode comprises ecogenic markings at known positions on their shafts so that when the combination of one of the at least two cannulas and said tissue piercing needle, or the combination of one of the at least two cannulas and said electrode are inserted into the patient's body tissue, an ultrasonic imaging machine can be used to visualize the position of portions of the cannula, and/or said tissue piercing needle, and/or said electrode relative to the structures in the patient's body.

57. The system of claim 54, wherein each of the at least two cannulas, and/or tissue piercing needle, and/or electrode comprises x-ray visible markings at known positions on their shafts so that when the combination of one of the at least two cannulas and said tissue piercing needle, or the combination of one of the at least two cannulas and said electrode are inserted into the patient's body tissue, an x-ray, fluoroscopy, CT, or other radiographic imaging machine can be used to visualize the position of portions of the cannula, and/or said tissue piercing needle, and/or said electrode relative to the structures in the patient's body.

58. An electrode system adapted for introduction into bodily tissue comprising:
   at least two cannulas of different lengths, each cannula having an internal lumen and having a cannula shaft portion to be inserted into the living body, the shaft portion being substantially insulated, and a cannula shaft portion having a cannula distal end and a cannula proximal end, the cannula distal end having an opening that connects to the internal lumen, and the cannula proximal end being immovably connected to a cannula hub;
   an insertion needle that is adapted to be inserted into the internal lumen of any of the at least two cannulas, the insertion needle having a needle shaft portion that has a needle distal end and a needle proximal end, a distal end of the insertion needle being adapted to pierce the tissue of the living body, and a proximal end of the insertion needle being immovably connected to a needle hub, and the needle shaft portion having a predetermined needle length so that when the needle shaft portion is inserted into a cannula internal lumen of one of the at least two cannulas so that the cannula hub and said needle hub are in a predetermined needle hub position relative to the cannula hub, the assembly of said insertion needle within the cannula is adapted to be inserted into the tissue of the living body, and said distal end of the insertion needle will extend beyond the cannula distal end by a predetermined extension distance greater 6 mm;
   wherein the predetermined extension distance is different for the at least two cannula;
   a high-frequency electrode that is adapted to be inserted into said internal lumen of any of the at least two cannulas, the high-frequency electrode having an electrode shaft portion that has an electrode distal end and an electrode proximal end, the electrode proximal end being immovably connected to an electrode hub, and the electrode shaft portion is substantially uninsulated, and the electrode shaft portion having a predetermined electrode length that is substantially equal to the needle length, so that when the electrode shaft portion is inserted into the cannula internal lumen of one of the at least two cannulas so that the cannula hub and said electrode hub are in a predetermined electrode hub position relative to the cannula hub, an uninsulated portion of said electrode shaft electrode extends beyond the cannula distal end and said electrode distal end extends beyond the cannula distal end by said predetermined extension distance, the distal end of said electrode directed along a tract that is the same as the tract as said insertion needle within said cannula so that said electrode distal end is located at the same target position;
   wherein the needle hub position is not predetermined by a set screw or a user-adjustable device, and the said electrode hub position is not predetermined by a set screw or a user-adjustable device; and
   wherein said electrode comprises an internal fluid channel, a fluid input port and a fluid output port; the input port being adapted to be connected to a source of coolant fluid so that the coolant fluid can flow into the input port, through the internal fluid channel, and out of the output port, whereby the electrode shaft portion is cooled by said coolant fluid.

59. The system of claim 58, wherein each of said at least two cannulas, and/or insertion needle, and/or high-frequency electrode comprises ecogenic markings at known positions on their shafts so that when the combination of one of said at least two cannulas and said insertion needle, or the combination of one of said at least two cannulas and said high-frequency electrode are inserted into the patient's body tissue, an ultrasonic imaging machine can be used to visualize the position of portions of the one of the at least two cannulas, and/or said insertion needle, and/or said high-frequency electrode relative to the structures in the patient's body.

60. The system of claim 58, wherein each of said at least two cannulas, and/or insertion needle, and/or high-frequency electrode comprises x-ray visible markings at known positions on their shafts so that when the combination of one of at least two cannulas and said insertion needle, or the combination of one of at least two cannulas and said high-frequency electrode are inserted into the patient's body tissue, an x-ray, fluoroscopy, CT, or other radiographic imaging can be used to visualize the position of portions of the at least two cannula, and/or said insertion needle, and/or said high-frequency electrode relative to the structures in the patient's body.

61. The electrode system of claim 23, wherein the cannula uninsulated portion of each of the at least two cannulas is substantially all of said combined exposed tip.

* * * * *